(12) United States Patent
Cox et al.

(10) Patent No.: US 8,034,296 B2
(45) Date of Patent: Oct. 11, 2011

(54) MICROFLUIDIC CARD FOR RBC ANALYSIS

(75) Inventors: James A. Cox, New Brighton, MN (US); Aravind Padmanabhan, Plymouth, MN (US); Ron L. Bardell, St. Louis Park, MN (US); Christopher J. Zins, Inver Grove Heights, MN (US)

(73) Assignee: Honeywell International Inc., Morristown, NJ (US)

( * ) Notice: Subject to any disclaimer, the term of this patent is extended or adjusted under 35 U.S.C. 154(b) by 1033 days.

(21) Appl. No.: 11/428,289

(22) Filed: Jun. 30, 2006

(65) Prior Publication Data

US 2007/0031289 A1 Feb. 8, 2007

Related U.S. Application Data

(60) Provisional application No. 60/696,162, filed on Jul. 1, 2005.

(51) Int. Cl.
*G01N 33/00* (2006.01)

(52) U.S. Cl. ...... 422/73; 422/69; 422/82.05; 422/82.09; 210/96.1; 210/511; 210/634

(58) Field of Classification Search ............... None
See application file for complete search history.

(56) References Cited

U.S. PATENT DOCUMENTS

| | | | |
|---|---|---|---|
| 3,822,095 A | 7/1974 | Hirschfeld | |
| 3,928,094 A | 12/1975 | Angell | |
| 3,976,862 A | 8/1976 | Curbelo | |
| 4,284,412 A | 8/1981 | Hansen et al. | |
| 4,478,076 A | 10/1984 | Bohrer | |
| 4,478,077 A | 10/1984 | Bohrer et al. | |
| 4,501,144 A | 2/1985 | Higashi et al. | |
| 4,599,000 A | 7/1986 | Yamada | |
| 4,651,564 A | 3/1987 | Johnson et al. | |
| 4,683,159 A | 7/1987 | Bohrer et al. | |
| 4,695,034 A | 9/1987 | Shimizu et al. | |
| 4,704,033 A | 11/1987 | Fay et al. | |

(Continued)

FOREIGN PATENT DOCUMENTS

DE 10122321 4/2002
(Continued)

OTHER PUBLICATIONS

Schilling, Eric, Basic Microfluidic Concepts, 2001, [online] Retrieved from the internet:<URL:http:/faculty.washington.edu/yagerp/microfluidicstutorial/basicconcepts/basicconcepts.htm>.*

(Continued)

*Primary Examiner* — Yelena G Gakh
*Assistant Examiner* — Robert Xu
(74) *Attorney, Agent, or Firm* — Seager, Tufte & Wickhem LLC

(57) ABSTRACT

A microfluidic circuit cartridge for a complete blood count, including analyses of red blood cells. Various parameters of the red blood cells may be attained. The cartridge may have sphering mechanism which has a channel or loop with a configuration for reducing or eliminating cell settling. The channel or loop may incorporate a combination of straight and curve paths in the context of gravity. The channel may alternatively have a hydrophilic or hydrophobic inside surface. Again alternatively, the channel may have an electrowettable inside surface. Or, the channel may be subject to an electric or magnetic field. There may also be a mechanism for reducing or eliminating clumping of a sample.

29 Claims, 40 Drawing Sheets

U.S. PATENT DOCUMENTS

| | | | |
|---|---|---|---|
| 4,745,279 A | 5/1988 | Karkar et al. | |
| 4,818,263 A | 4/1989 | Mitch | |
| 4,874,949 A | 10/1989 | Harris et al. | |
| 4,911,616 A | 3/1990 | Laumann, Jr. | |
| 4,932,989 A | 6/1990 | Presby | |
| 5,017,497 A | 5/1991 | Gerard de Grooth et al. | |
| 5,050,429 A | 9/1991 | Nishimoto et al. | |
| 5,078,581 A | 1/1992 | Blum et al. | |
| 5,082,242 A | 1/1992 | Bonne et al. | |
| 5,085,562 A | 2/1992 | van Lintel | |
| 5,096,388 A | 3/1992 | Weinberg | |
| 5,108,623 A | 4/1992 | Cangelosi et al. | |
| 5,129,794 A | 7/1992 | Beatty | |
| 5,171,132 A | 12/1992 | Miyazaki et al. | |
| 5,176,358 A | 1/1993 | Bonne et al. | |
| 5,185,641 A | 2/1993 | Igushi et al. | |
| 5,194,909 A * | 3/1993 | Tycko | 356/40 |
| 5,219,278 A | 6/1993 | van Lintel | |
| 5,224,843 A | 7/1993 | van Lintel | |
| 5,230,866 A | 7/1993 | Shartle et al. | |
| 5,244,537 A | 9/1993 | Ohnstein | |
| 5,323,999 A | 6/1994 | Bonne et al. | |
| 5,350,695 A | 9/1994 | Colella et al. | |
| 5,441,597 A | 8/1995 | Bonne et al. | |
| 5,452,878 A | 9/1995 | Gravesen et al. | |
| 5,457,526 A | 10/1995 | Kosaka | |
| 5,510,267 A | 4/1996 | Marshall | |
| 5,528,045 A | 6/1996 | Hoffman et al. | |
| 5,570,193 A | 10/1996 | Landa et al. | |
| 5,601,080 A | 2/1997 | Oppenheimer | |
| 5,616,501 A | 4/1997 | Rodriguez et al. | |
| 5,633,724 A | 5/1997 | King et al. | |
| 5,683,159 A | 11/1997 | Johnson | |
| 5,716,852 A | 2/1998 | Yager et al. | |
| 5,717,631 A | 2/1998 | Carley et al. | |
| 5,726,751 A | 3/1998 | Altendorf et al. | |
| 5,757,476 A | 5/1998 | Nakamoto et al. | |
| 5,760,900 A | 6/1998 | Ito et al. | |
| 5,793,485 A | 8/1998 | Gourley | |
| 5,799,030 A | 8/1998 | Brenner | |
| 5,822,170 A | 10/1998 | Cabuz et al. | |
| 5,836,750 A | 11/1998 | Cabuz | |
| 5,839,807 A | 11/1998 | Perlo | |
| 5,863,502 A | 1/1999 | Southgate et al. | |
| 5,880,474 A | 3/1999 | Norton et al. | |
| 5,893,722 A | 4/1999 | Hibbs-Brenner et al. | |
| 5,901,939 A | 5/1999 | Cabuz et al. | |
| 5,922,210 A | 7/1999 | Brody et al. | |
| 5,932,100 A | 8/1999 | Yager et al. | |
| 5,948,684 A | 9/1999 | Weigl et al. | |
| 5,970,315 A | 10/1999 | Carley et al. | |
| 5,971,158 A | 10/1999 | Yager et al. | |
| 5,972,710 A | 10/1999 | Weigl et al. | |
| 5,974,867 A | 11/1999 | Forster et al. | |
| 6,007,775 A | 12/1999 | Yager | |
| 6,032,689 A | 3/2000 | Tsai et al. | |
| 6,054,335 A | 4/2000 | Sun et al. | |
| 6,082,185 A | 7/2000 | Saaski | |
| 6,091,197 A | 7/2000 | Sun et al. | |
| 6,091,537 A | 7/2000 | Sun et al. | |
| 6,094,293 A | 7/2000 | Yokoyama et al. | |
| 6,097,485 A | 8/2000 | Lievan | |
| 6,097,859 A | 8/2000 | Solgaard et al. | |
| 6,106,245 A | 8/2000 | Cabuz | |
| 6,109,889 A | 8/2000 | Zengerle et al. | |
| 6,116,756 A | 9/2000 | Peeters et al. | |
| 6,124,663 A | 9/2000 | Haake et al. | |
| 6,139,800 A | 10/2000 | Chandler | |
| 6,179,586 B1 | 1/2001 | Herb et al. | |
| 6,184,607 B1 | 2/2001 | Cabuz et al. | |
| 6,215,221 B1 | 4/2001 | Cabuz et al. | |
| 6,237,619 B1 | 5/2001 | Maillefer et al. | |
| 6,240,944 B1 | 6/2001 | Ohnstein et al. | |
| 6,249,341 B1 | 6/2001 | Basiji et al. | |
| 6,270,641 B1 * | 8/2001 | Griffiths et al. | 204/451 |
| 6,281,975 B1 | 8/2001 | Munk | |
| 6,382,228 B1 | 5/2002 | Cabuz et al. | |
| 6,549,275 B1 | 4/2003 | Cabuz et al. | |
| 6,597,438 B1 | 7/2003 | Cabuz et al. | |
| 6,712,925 B1 | 3/2004 | Holl et al. | |
| 6,729,856 B2 | 5/2004 | Cabuz et al. | |
| 6,733,244 B1 * | 5/2004 | Fritsch et al. | 417/48 |
| 6,767,190 B2 | 7/2004 | Cabuz et al. | |
| 6,877,892 B2 * | 4/2005 | Karp | 366/341 |
| 6,970,245 B2 | 11/2005 | Fritz et al. | |
| 7,273,590 B2 * | 9/2007 | Yao et al. | 422/100 |
| 7,344,681 B1 * | 3/2008 | Fiechtner et al. | 422/100 |
| 7,497,997 B2 | 3/2009 | Glezer et al. | |
| 2002/0149766 A1 * | 10/2002 | Bardell et al. | 356/246 |
| 2002/0182627 A1 | 12/2002 | Wang et al. | |
| 2003/0142291 A1 | 7/2003 | Padmanabhan et al. | |
| 2004/0070757 A1 | 4/2004 | Moore et al. | |
| 2004/0132218 A1 | 7/2004 | Ho | |

FOREIGN PATENT DOCUMENTS

| | | |
|---|---|---|
| DE | 10320870 | 12/2004 |
| EP | 0269076 | 6/1988 |
| EP | 1001326 | 5/2000 |
| EP | 1134548 | 9/2001 |
| EP | 1388366 | 2/2004 |
| EP | 1542010 | 6/2005 |
| JP | 61066947 | 4/1986 |
| JP | 10073528 | 3/1998 |
| JP | 2000056228 | 2/2000 |
| WO | 9527199 | 10/1995 |
| WO | 9960397 | 11/1999 |
| WO | 0109598 | 2/2001 |
| WO | 0210713 | 2/2002 |
| WO | 0210714 | 2/2002 |

OTHER PUBLICATIONS

Lo, Yi-Chung, et al., Neural Guidance by Open-Top SU-8 Microfluidic Channel, 2004, Proceedings of the 2004 International Conference on MEMS, NANO and Smart Systems (ICMENS'04).*

Fowler et al, "Enhancement of Mixing by Droplet-Based Microfluidics," IEEE, pp. 97-100, 2002.

http://www.micronics.net/tsensor.htm, pp. 1-4, downloaded Jun. 14, 2000.

http://www.micronics.net/hfilter.htm, pp. 1-3, downloaded Jun. 14, 2000.

http://www.micronics.net/mcytometry.htm, pp. 1-4, downloaded Jun. 14, 2000.

http://www.micronics.net/orcafluidics.htm, pp. 1-4, downloaded Jun. 14, 2000.

Altendorf et al, "Results Obtained Using a Prototype Microfluidics-Based Hematology Analyzer", SPIE Biomedical Optics 97, 1997.

* cited by examiner a) Initial section b) Section i

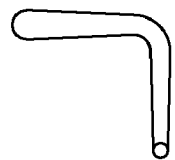
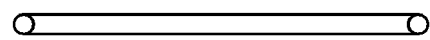
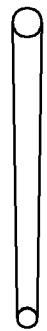
Figure 6

| Layer Number | Material | Nominal Thickness {mils} | Thickness Range of Material {mils} | Allowable Total Variation Between Cards Within 1 Lot {mils (mm)} |
|---|---|---|---|---|
| 41 | PMMA | 60 | 54<t<66 | 7.5 (0.190) |
| 42 | ACA | 6 | 5.4<t<6.6 | 0.6 (0.015) |
| 43 | PET | 2 | 1.98<t<2.02 | 0.04 (0.001) |
| 44 | Green ACA | 4 | 3.9<t<4.1 | 0.2 (0.005) |
| 45 | PET | 2 | 1.98<t<2.02 | 0.04 (0.001) |
| 46 | ACA | 6 | 5.4<t<6.6 | 0.6 (0.015) |
| 47 | PMMA | 120 | 110<t<130 | 10 (0.254) |
| 48 | ACA | 6 | 5.4<t<6.6 | 1.2 (0.030) |
| 49 | PMMA | 60 | 54<t<66 | 12 (0.300) |

Figure 20

| Fluid | Dilution | Stage 1 {µl/min} | Stage 2 {µl/min} | Sphering channel minimum volume {µl} |
|---|---|---|---|---|
| Sample | None | 3 | 0 | N.A. |
| Sphering solution | 600 to 1 | 1800 | 21.6 | 3.6 |
| Sphering solution | 300 to 1 | 900 | 10.8 | 1.8 |
| Sphering solution | 200 to 1 | 600 | 7.2 | 1.2 |
| Sphering solution | 100 to 1 | 300 | 3.6 | 0.6 |

Figure 21

| Dilution | Stage 1 diluent flow rate {µl/min} | Cell coincidence {%} | Sphered RBC solution storage {µl} |
|---|---|---|---|
| 600 to 1 | 1800 | 2.5 | 3.6 |
| 300 to 1 | 900 | 4.8 | 1.8 |
| 200 to 1 | 600 | 6.5 | 1.2 |
| 100 to 1 | 300 | >15 | 0.6 |

Figure 23

| Dilution | Sample flow rate {μl/min} | Stage 1 diluent flow rate {μl/min} = Sheath flow rate | Cell coincidence {%} | Sampling time for 15,000 counts {sec} | Sphered RBC solution stored in 10 seconds {μl} |
|---|---|---|---|---|---|
| 333 to 1 | 1.5 | 500 | 1.5 | 60 | 83 |
| 267 to 1 | 1.5 | 400 | 2.2 | 48 | 67 |
| 167 to 1 | 3 | 500 | 2.8 | 30 | 83 |
| 133 to 1 | 3 | 400 | 4 | 24 | 67 |

Figure 25

MICROFLUIDIC CARD FOR RBC ANALYSIS

The present invention claims the benefit of U.S. Provisional Patent Application No. 60/696,162, filed Jul. 1, 2005. U.S. Provisional Patent Application No. 60/696,162, filed Jul. 1, 2005, is hereby incorporated by reference.

BACKGROUND

The present invention pertains to analyzers and particularly to hematology analyzers. More particularly, the invention pertains to analyzers with removable cards or cartridges.

Patents and applications related to the present invention may include: U.S. Pat. No. 6,382,228, issued May 7, 2002, and entitled "Fluid Driving System for Flow Cytometry"; U.S. Pat. No. 6,597,438, issued Jul. 22, 2003, and entitled "Portable Flow Cytometry"; U.S. Pat. No. 6,970,245, issued Nov. 29, 2005, and entitled "Optical Alignment Detection System; U.S. Pat. No. 6,549,275, issued Apr. 15, 2003, and entitled "Optical Detection System for Flow Cytometry"; U.S. Pat. No. 5,836,750, issued Nov. 17, 1998, and entitled "Electrostatically Actuated Mesopump Having a Plurality of Elementary Cells"; U.S. patent application Ser. No. 11/027,134, filed Dec. 30, 2004, and entitled "Optical Detection System with Polarizing Beamsplitter; U.S. patent application Ser. No. 10/908,543, filed May 16, 2005, and entitled "Cytometer Analysis Cartridge Optical Configuration"; and U.S. patent application Ser. No. 10/908,014, filed Apr. 25, 2005, and entitled "A Flow Control System of a Cartridge"; all of which are hereby incorporated by reference.

SUMMARY

This invention describes a microfluidic card system for the measurement of some red blood cell indices as part of a blood count measurement. The system may include microfluidic structures to reduce or eliminate sample clumping and/or particle settling.

BRIEF DESCRIPTION OF THE DRAWING

FIGS. 4-12 shown certain layers of the analysis card;

FIG. 20 is a table of dimensions of layers of the card;

FIG. 21 is table of dilution and sphering specifications of the sample;

FIG. 23 shows a table with parameters of diluent flow rate, cell coincidence and solution storage;

FIG. 25 shows a table with parameters of diluent flow rate, cell coincidence and solution storage;

DESCRIPTION

Figure 1A:
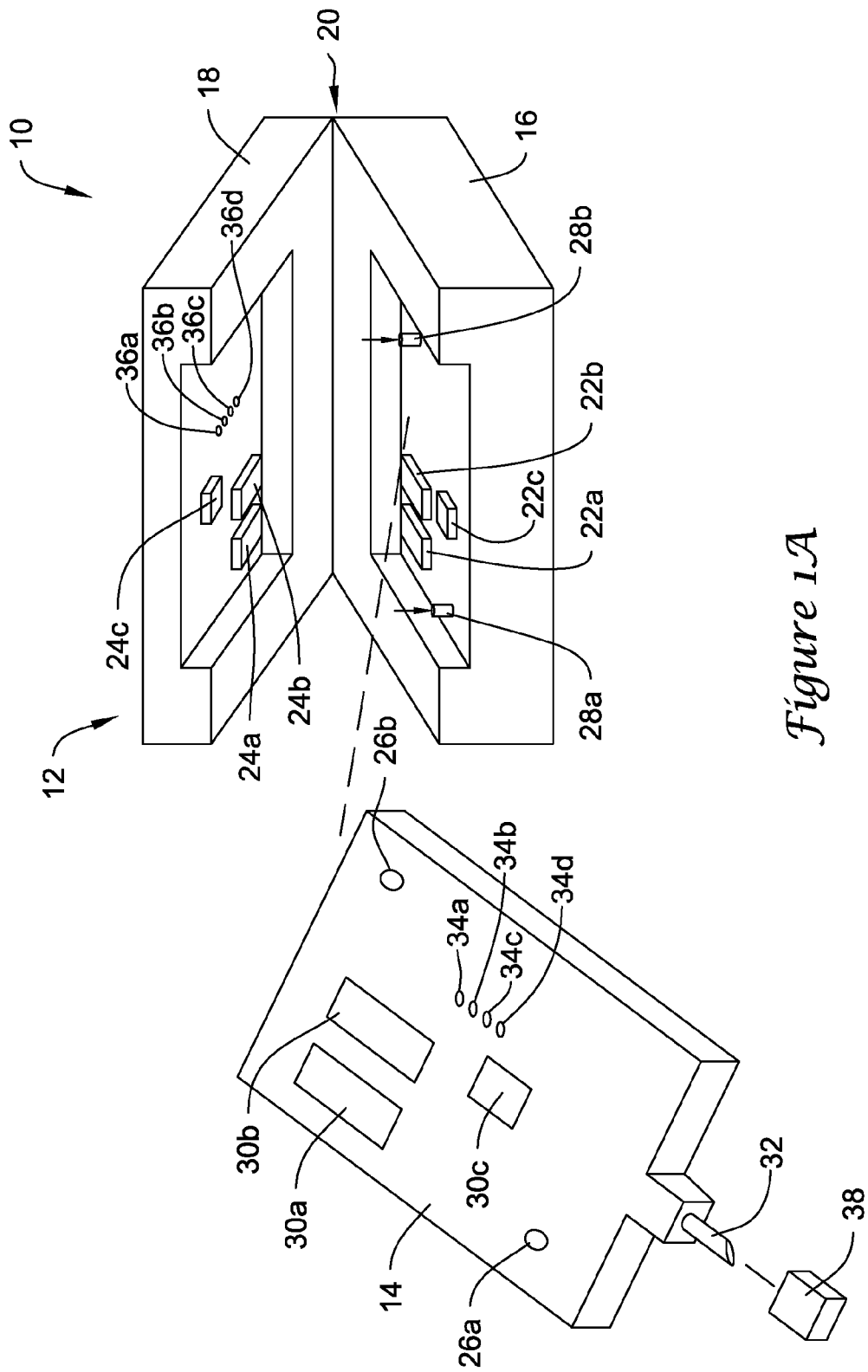
FIG. 1a is a diagram of a hematology analysis system.

The present invention generally relates to sample analyzers, and in particular, to sample analyzers or cytometers with removable and/or disposable cartridges for use at the point of care of a patient such as in a doctor's office, in the home, or elsewhere in the field. By providing a removable and/or disposable cartridge or card with the needed reagents and/or fluids, the sample analyzer may be reliably used outside of the laboratory environment, with little or no specialized training. The present analyzer may, for example, help streamline the sample analysis process, reduce the cost and burden on medical or other personnel, and increase the convenience of sample analysis for many patients, including those that require relatively frequent blood monitoring/analysis.

An approach which allows rapid and efficient particle discrimination in a particle-suspension sample is flow cytometry. In this approach, a suspension of particles, typically cells in a blood sample, is transported through a flow channel where the individual particles in the sample are illuminated with one or more focused light beams. The interaction of the light beam(s) with the individual particles flowing through the flow channel is detected by one or more light detectors. Commonly, the detectors are designed to measure light absorption or fluorescence emission, at specific beam or emission wavelengths, and/or light scattering at specific scattering angles. Thus, each particle that passes through the flow channel can be characterized as to one or more features related to its absorption, fluorescence, light scattering or other optical or electrical properties. The properties that are measured by the detectors may allow each particle to be mapped into a feature space whose axes are the light intensities or other properties which are measured by the detectors. In an ideal situation, the different particles in the sample may map into distinct and non-overlapping regions of the feature space, allowing each particle to be analyzed based on its mapping in the feature space. Such analysis may include counting, identifying, quantifying (as to one or more physical characteristics) and/or sorting of the particles.

In one illustrative example, there may be a sample analyzer which is provided that has a removable cartridge that receives a collected sample, such as a collected whole blood sample, and once the removable cartridge is installed and the analyzer is activated, the analyzer and cartridge may automatically process the sample and the analyzer may provide sufficient information for the user to make a clinical decision. In some examples, the analyzer may display or print out quantitative results (e.g., inside and/or outside of a predefined range), such that no further calculations or interpretation is required by the user.

The sample analyzer may be used, for example, to determine the number and/or types of blood cells in a blood sample. In an illustrative example, the analyzer includes a housing and a removable fluidic cartridge, wherein the housing is adapted to receive the removable fluidic cartridge. In some cases, the removable fluidic cartridge is a disposable cartridge. In an illustrative example, the removable fluidic cartridge may include one or more reagents (e.g., sphering agents, lysing reagents, sheathing agents, stain, and/or diluents, one or more analysis channels, one or more flow sensors, one or more valves, and/or a fluidic circuit that is adapted to process (e.g., sphere, lyse, sheath, stain, or other) a sample and deliver processed sample(s) to the appropriate analysis channel on the cartridge. To support the card, the housing may include, for example, a pressure source, one or more light sources, one or more light detectors, a processor and a power source. The pressure source may provide appropriate pressure(s) to the removable fluidic cartridge ports to drive the fluids as required through the fluidic circuit. The one or more light sources of the analyzer may be used to interrogate the prepared sample in at least selected analysis channels of the removable cartridge, and the one or more light detectors of the analyzer may detect the light that passes through, is absorbed by and/or is scattered by the sample. The processor may be coupled to at least some of the light sources and detectors, and possibly flow sensors, valves and/or pumps, and may determine one or more parameters of the sample. In some examples, the one or more analysis channels on the removable fluidic cartridge may include one or more flow cytometry channels. In some illustrative examples, a whole blood sample may be provided to the removable fluidic cartridge, and the removable cartridge may be adapted to perform a blood analysis.

The present system may provide a complete blood count (CBC) card based on a micro-scale flow cytometer for obtaining one or more of the following items including red blood cell (RBC) counts, sphering RBCs, platelet counts, lysis of RBCs, mean cell volume determinations of RBCs, multi-part differential counts of white blood cells (WBCs), hemoglobin absorbence-based measurements, various additional indices of RBCs, platelets, WBCs, hemoglobin, and so forth, plus hydrodynamic focusing to create single-file streams of cells, and a pneumatic fluid driver system. Additional items may be provided by and/or be a part of the present system.

To obtain cards for functionality testing, a card for testing the measurement and count of RBCs and platelets may be used. This card may employ a wet interface with fluids supplied by volumetric-based delivery from an off-card reagent storage and flow sensors. The only on-card storage retained may be the waste tank and the whole blood sample loop.

FIG. 1a is a perspective view of an illustrative sample analyzer and cartridge. The illustrative sample analyzer is generally shown at 10, and may include a housing 12 and a removable or disposable cartridge 14. Cartridge or card 14 may be for a red blood count (RBC) with an anti-sediment channel as noted herein. The illustrative housing 12 may include a base 16, a cover 18, and a hinge 20 that attaches the base 16 to the cover 18, but this is not required. In the illustrative example, the base 16 includes a first light source 22a, a second light source 22b, and a third light source 22c, along with associated optics and the necessary electronics for operation of the sample analyzer. Each of the light sources may be a single light source or multiple light sources, depending on the application. In some cases, the overall dimensions of the housing may be less than 1 cubic foot, less than one-half cubic foot, less than one-quarter cubic foot, or smaller, as desired. Likewise, the overall weight of the housing may be less than 10 pounds, less than 5 pounds, less than one pound, or less, as desired.

The illustrative cover 12 may include a pressure source (e.g. pressure-chambers with control microvalves), a first light detector 24a, a second light detector 22b, and a third light detector 22c, each with associated optics and electronics, e.g., a processor. Each of the light detectors may also be a single light detector or multiple light detectors, depending on the application. Polarizers, splitters, and/or filters may also be provided, if desired, depending on the application.

The illustrative removable cartridge 14 may be adapted to receive a sample fluid via a sample collector port, which in the illustrative example, includes a lancet 32. The lancet 32 may be retractable and/or spring loaded, as in some examples. A cap 38 may be used to protect the sample collector port and/or lancet 32 when the removable cartridge 14 is not in use.

In the illustrative example, the removable cartridge 14 may perform a blood analysis on a whole blood sample. The lancet 32 may be used to prick the finger of the user to produce a sample of blood, which through capillary action, may be drawn into an anti-coagulant coated capillary in the removable cartridge 14. The removable cartridge 14 may be constructed with fluidic circuits, some of which are fabricated using a laminated structure with etched channels. However, it is contemplated that the removable cartridge 14 may be constructed in any suitable manner including by injection molding or any other suitable manufacturing process or method, as desired.

During use, and after a blood sample has been drawn into the removable cartridge 14, the removable cartridge 14 may be inserted into the housing when the cover 18 is in the open position. In some cases, the removable cartridge 14 may include holes 26a and 26b for receiving registration pins 28a and 28b in the base 16, which may help provide alignment and coupling between the different parts of the instrument. The removable cartridge 14 may also include a first transparent flow stream window 30a, a second transparent flow stream window 30b and a third transparent window 30c, which are in alignment with the first, second and third light sources 22a, 22b and 22c, and the first, second and third light detectors 24a, 24b and 24c, respectively.

When the cover is moved to the closed position, and the system is pressurized, the cover 18 may provide controlled pressures via pressure providing ports 36a, 36b, 36c, and 36d to pressure receiving ports 34a, 34b, 34c and 34d, respectively, in the illustrative removable cartridge 14. It is contemplated that more or less pressure providing and pressure receiving ports may be used, depending on the application. Alternatively, or in addition, it is contemplated that one or more micro-pumps, such as electrostatically actuated meso pumps, may be provided on or in the removable cartridge 14 to provide the necessary pressures to operate the fluidic circuit on the removable cartridge 14. Some illustrative electrostatically actuated meso pumps may be described in, for example, U.S. Pat. Nos. 5,836,750, 6,106,245, 6179,586, 6,729,856, and 6,767,190, all assigned to the assignee of the present invention, and all incorporated herein by reference. Once pressurized, the illustrative instrument may perform a blood analysis on the collected blood sample.

Figure 1B:
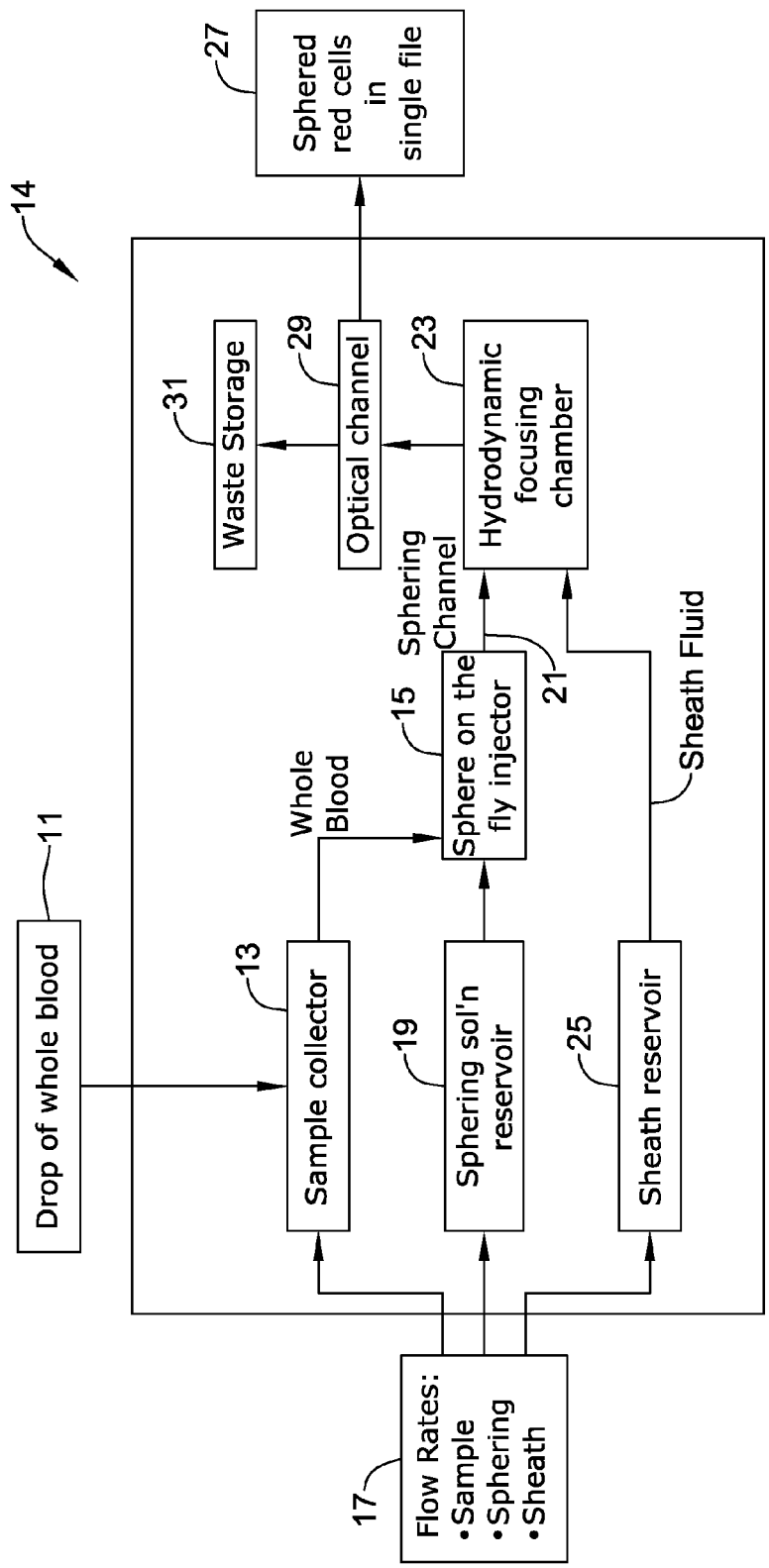
FIG. 1b is a diagram of an example red blood cell cartridge or card of the analysis system.

FIG. 1b is a diagram showing some aspects of an illustrative example RBC cartridge or card 14. One may start with a sample of whole blood 11 to a sample collector 13. The blood may be pushed on to a sphere on the fly injector 15. The flow rates for pushing the sample, and also for the sphering and sheathing fluids may be provided by pump mechanisms or flow rates control box 17. Sphering fluid for the sphere on the fly injector 15 may come from a sphering solution reservoir 19. The solution and blood may proceed through a sphering channel 21 to a hydrodynamic focusing chamber 23. A sheathing fluid may go from a sheath reservoir 25 to the hydrodynamic focusing chamber 23 to aid in aligning the sphered red cells in single file 27 through an optical channel 29 for detection and analysis. After the cells have proceeded through optical channel 29, the cells and fluid may proceed on to a waste storage 31.

The present system may be used to count and discriminate cells (e.g., RBCs, PLTs, and the like) and measure cell size (diameter, volume) in a cytometer channel using optical sensing. A laser (or other) source may be focused into a cytometer or flow channel, either as an elongated line source or as two separate spot sources. The cells may be made to flow in the cytometer channel through the focused light.

Several main or major parameters (e.g., indices), a red blood cell (RBC) count (cells/µL), a platelet (PLT) count (cells/µL), a mean cell volume (MCV), and a red cell distribution width (RDW) may be attained with an optical approach upon a blood sample. MCV is effectively a measurement of the average size of the RBCs. RDW is the variation of the size among the RBCs. A greater variation of the sizes of the RBCs, the greater is the RDW.

An RBC count is an actual number of RBCs per unit volume of the blood under analysis. Hct is hematocrit which is RBC×MCV, and may amount to a measure of oxygen carrying capacity of the blood (i.e., total capacity of all of the cells in the unit volume under analysis). Hct may also be regarded as an amount of space that the RBCs take up in the blood, or the proportion of the whole blood that is composed of red blood cells. MCH is the "mean cell hemoglobin" which is effectively the amount of hemoglobin in each RBC. MCH may be regarded as the mean or approximately an average mass of hemoglobin in an individual RBC, in units of picograms. MCH=Hb÷RBC. Hb is the amount of hemoglobin per unit volume of the sample under analysis. MCHC is the "mean cell hemoglobin concentration" which may be regarded as the concentration of hemoglobin per unit volume in each of the RBCs. MCHC=Hb÷Hct.

System may provide information via the control electronics or processor from essentially optical techniques including a set of measured parameters which include cell flow rate (FR), measurement time (T), dilution factor (DF), number of RBCs counted ($N_{RBC}$), number of platelets counted ($N_{PLT}$), the amount of hemoglobin (Hb), and the diameter (microns) of virtually each cell$_i$ (drbc$_i$). <drbc$_i$> is the average of the measured cell diameters of the cells, denoted by the set {drbc$_i$}. Some of the major calculated parameters may include: RBC=$N_{RBC}$÷(DF×FR×T); PLT=$N_{PLT}$÷(DF×FR×T); MCV=($\pi$/6)×<drbc$_i^3$>; and RDW=SD{[($\pi$/6)drbc$_i^3$]}÷MCV, where SD denotes the standard deviation of the measured quantities. Calculated parameters may include: Hct=RBC×MCV; MCHC=Hb÷Hct; and MCH=MCHC×MCV.

The blood sample may go on to a sample preparation module. The red blood cells may be turned from non-spheric shapes into spheres. The original shape of a red blood cell tends to be a flat cupped shape. This reshaping may be referred to as isovolumetric sphering. A sphering fluid may be used for reshaping the red blood cells into sphere-like cells, as described, for example, by Ornstein and Kim in U.S. Pat. No. 4,412,004. The sphering fluid appears to just affect the red blood cells of the sample.

One of the approaches involves a red blood count (RBC) card. One concern is attaining precise control of fluid flow rates and distribution of erythrocytes within the flow channels. One aiding property may be system stiffness. Good flow rate control, even with flow sensors off-card, is possible if the system has very low mechanical and fluidic compliance. This may require a mechanically stiff card, for example a card with thick walls.

Another concern is the sample loop. Channels with small cross-sections connected by small vias may provide the following properties. They may include increased flow resistance to increase backpressure, which reduces sample pushback, improved sweep-out of the sample by pusher fluid, increased mechanical stiffness by smaller channel walls, and increased fluidic stiffness by reduction in size and number of gas bubbles trapped during wet-out. Also, small wall roughness may minimize trapped bubbles.

Settling physics in the sphering channel may be noted. Erythrocytes have a specific gravity of approximately 1.1 and begin to settle immediately in diluted blood. The settling velocity $U_{settling}$ is a function of fluid viscosity, particle size and shape, and densities of the particle and fluid. For example, the settling velocity of a hard sphere in a Newonian fluid is $$U_{settling} = (2/9)a^2 \Delta \rho g / \mu$$

where a is the sphere radius, g is the acceleration of gravity, µ is the fluid viscosity, and $\Delta \rho$ is the density difference between the sphere and the surrounding fluid. Other particle shapes may have different settling velocities that are derived from the balance of frictional drag force and buoyancy force.

The local number density of cells at any location in the channel may be affected by settling. In cytometry, the particles are generally placed at the center of the channel. Particle sedimentation may adversely affect particle count accuracy by trapping particles along the wall and thus such particles will not be counted.

Figure 2A:
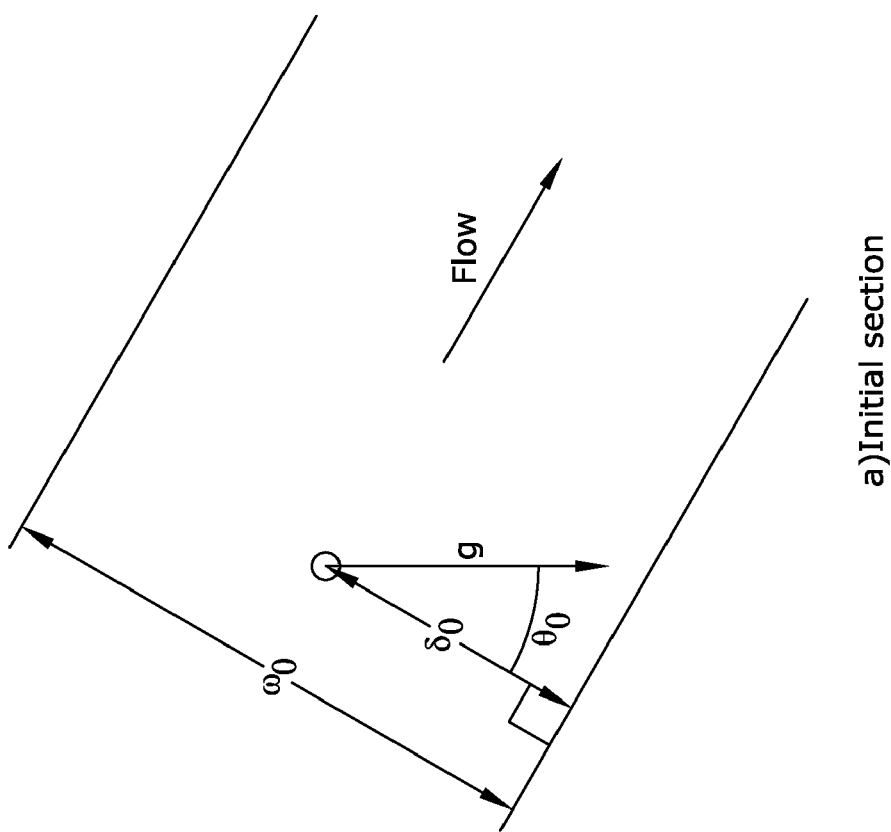
FIGS. 2a and 2b note an effect of gravity on particles in a channel and the channel direction relative to gravity.
Figure 2B:
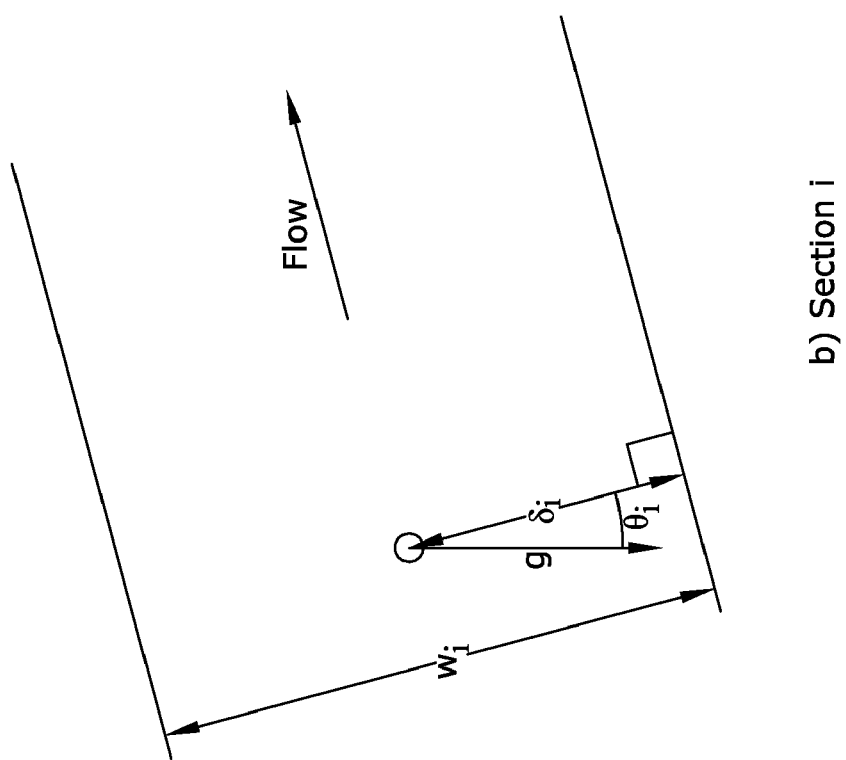

One strategy to avoid sedimentation may include rotating the direction of the channel flow with respect to the direction of gravity. This strategy may allow an increased residence time of the particle within the channel without sedimenting. A dimensionless sedimentation parameter, S, may be defined by $$S = (\delta_0/w_0) - (U_{Settling}/w) \Sigma_i (\cos \theta_i \Delta t_i) > 0$$

where which $\delta_0$ is the initial distance of the particle from the wall and w is the local width of a varying-width channel (FIGS. 2a and 2b for the initial and "i" sections, respectively). The subscript 0 refers to the initial values at the beginning of the channel and the subscript i=0, 1, 2, . . . , refers to each change in channel direction. The sigma notation $\Sigma$ stands for the summation of the following quantity in parentheses over each value of subscript i. The angle $\theta$ is the included angle between the direction of gravity and a line through the particle that is perpendicular to the wall. The time $\Delta t_i$ is the amount of time that a particle that is a distance $\delta$ from the wall will take to pass through section i of the channel. A positive value of S may ensure that the particle will not touch the wall.

FIGS. 2a and 2b are sketches of a particle in the initial section and a downstream section "i" of a fluid channel showing included angle $\theta$ between gravity direction g and distance of particle from wall $\delta$. The width of the channel w may change from section to section as well as the channel direction with respect to gravity. Changing channel direction may increase allowable residence time of particle within channel without particle sedimentation along the channel wall.

Relative to the sphering operation (i.e., serial dilution), the sphering channel may be loaded by a large diluent flow that sheathes a small sample flow. The loaded fluid may then be dispensed by the small flow of the sample.

Figure 3:
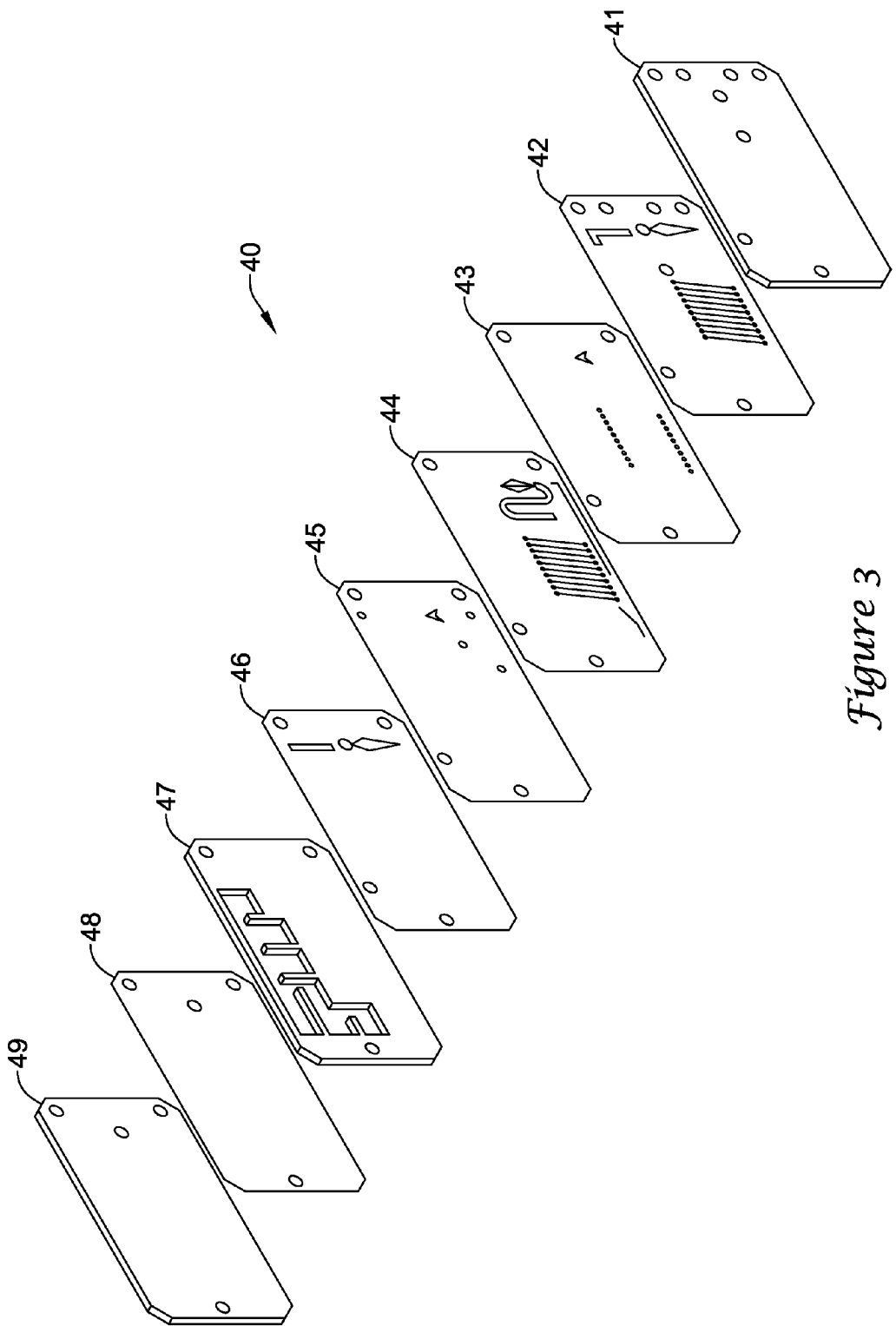
FIG. 3 is an exploded view of an analysis card.

FIG. 3 shows layers 41, 42, 43, 44, 45, 46, 47, 48 and 49 of an RBC card 40 apart from one another for illustrative purposes. FIGS. 4, 5, 6, 7, 8, 9, 10, 11 and 12 are dimensioned drawings showing layers of a cytometer card design. A datum may be defined at the optical channel 53. The dimensions may be specified with respect to the datum. The general tolerance may be within 10 percent on the features. Specific tolerances may be called out where tighter tolerances are desired.

Figure 4:
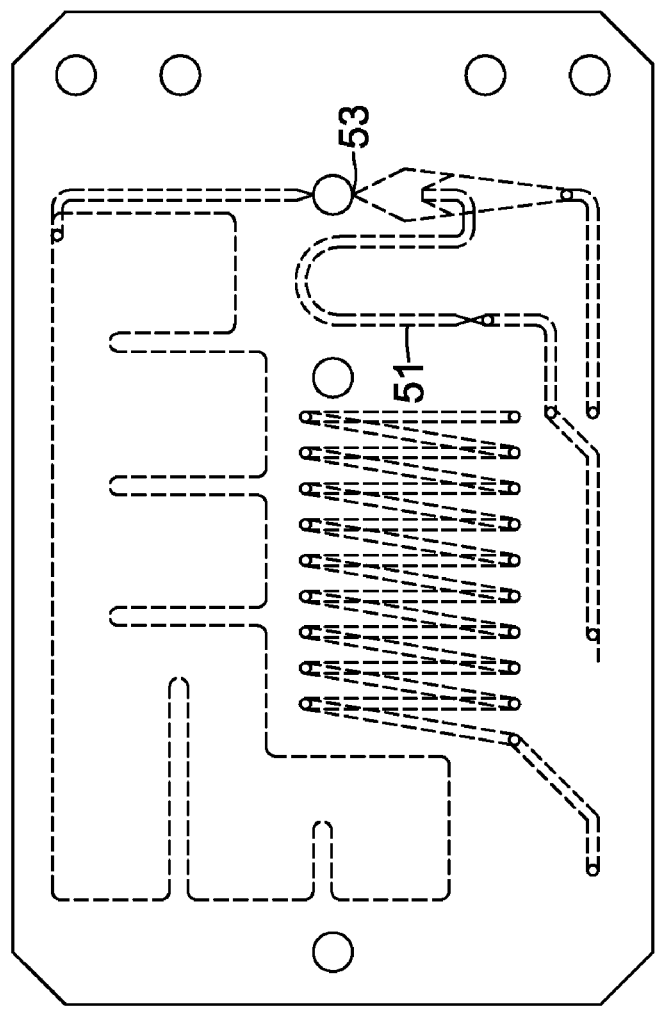
Figure 5:
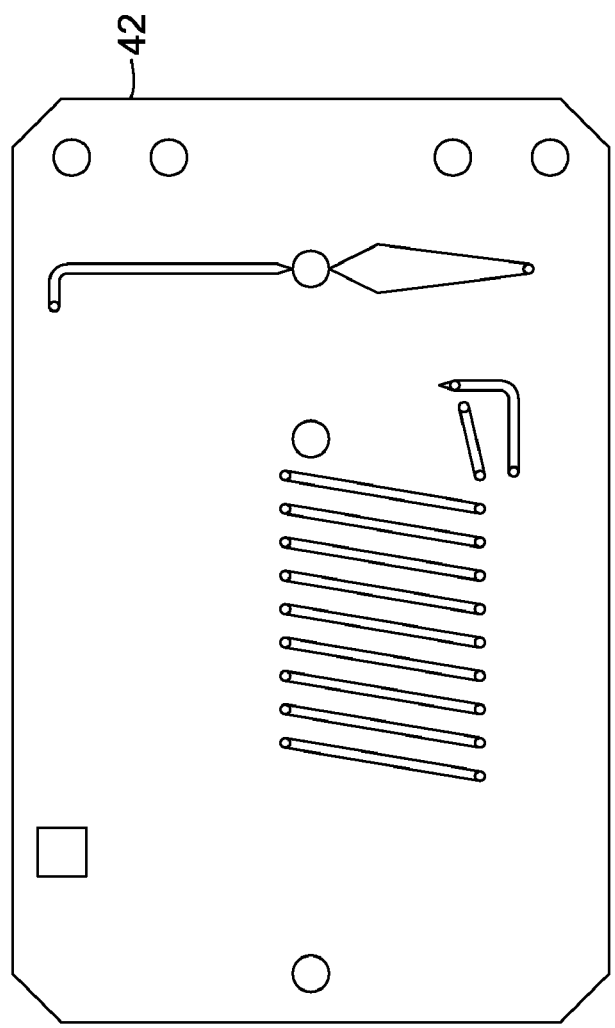
Figure 7:
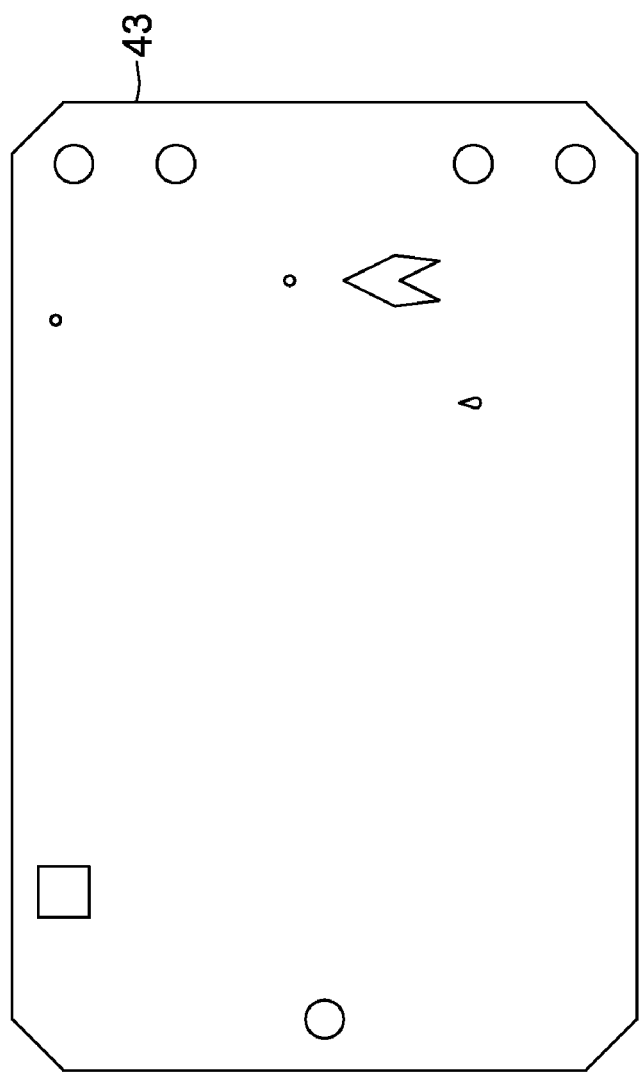
Figure 8:
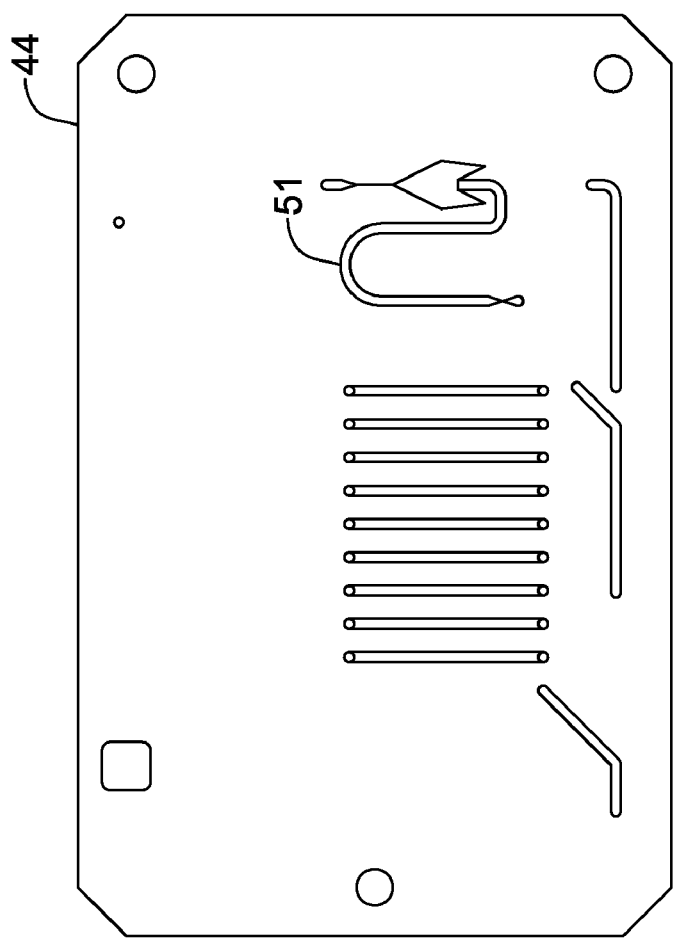
Figure 9:
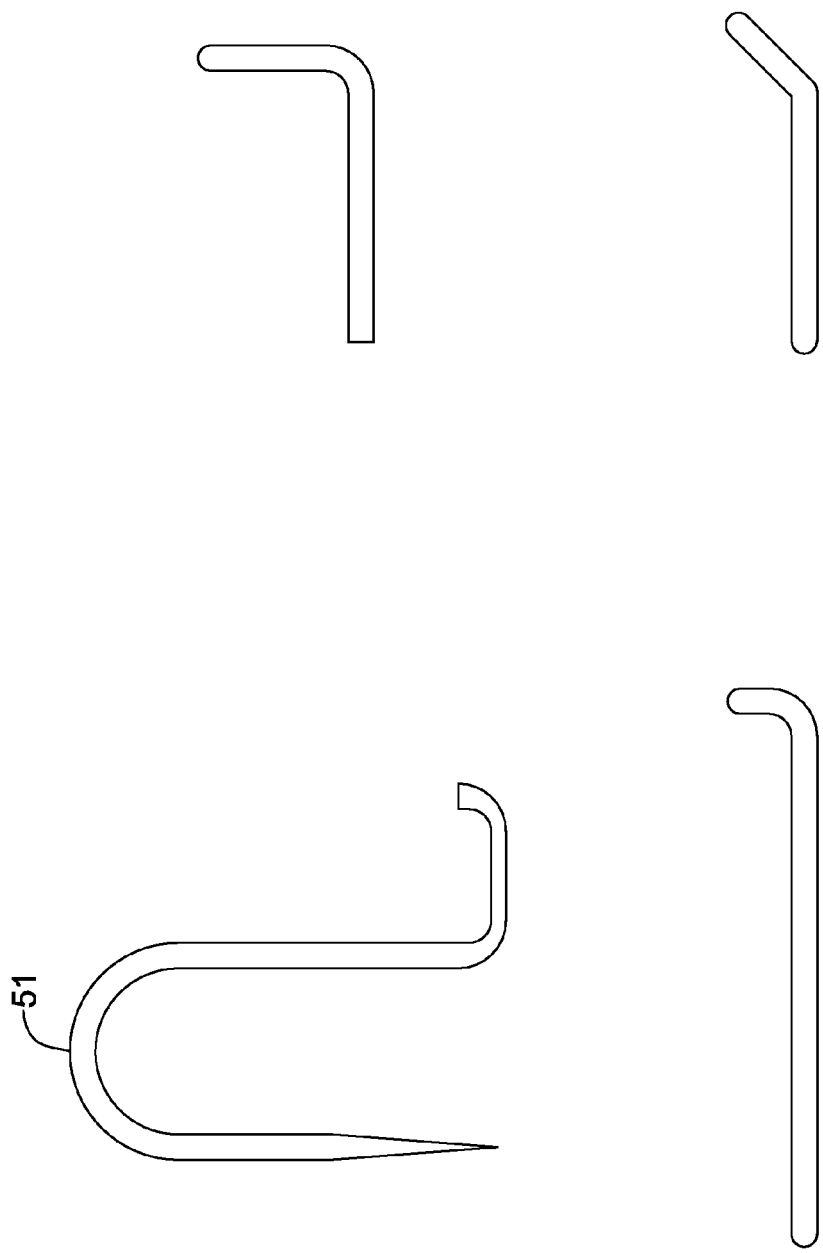
Figure 10:
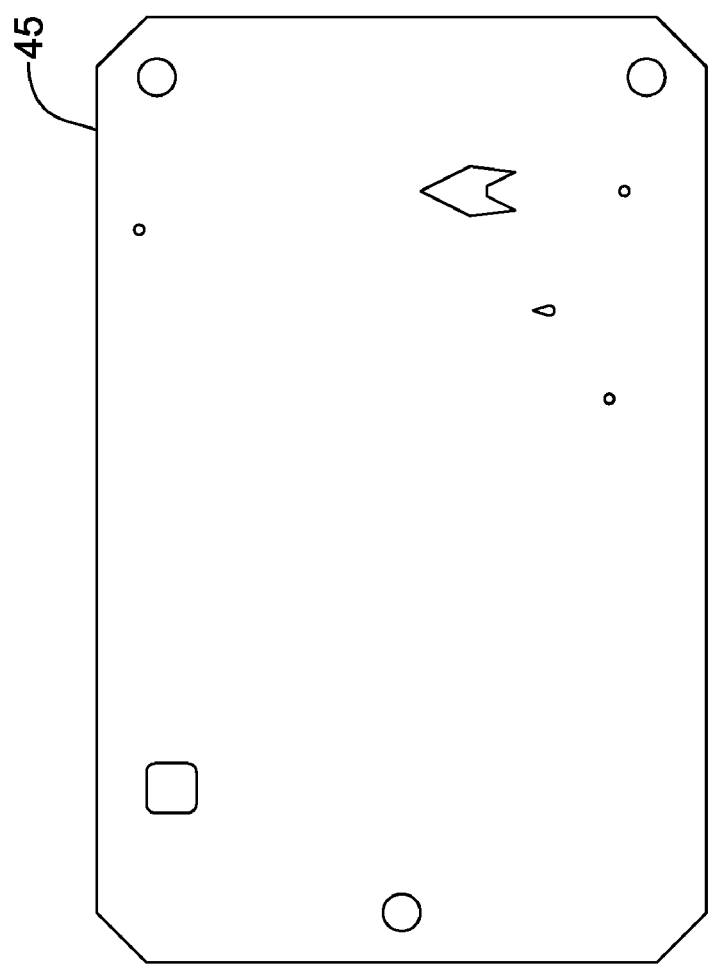
Figure 11:
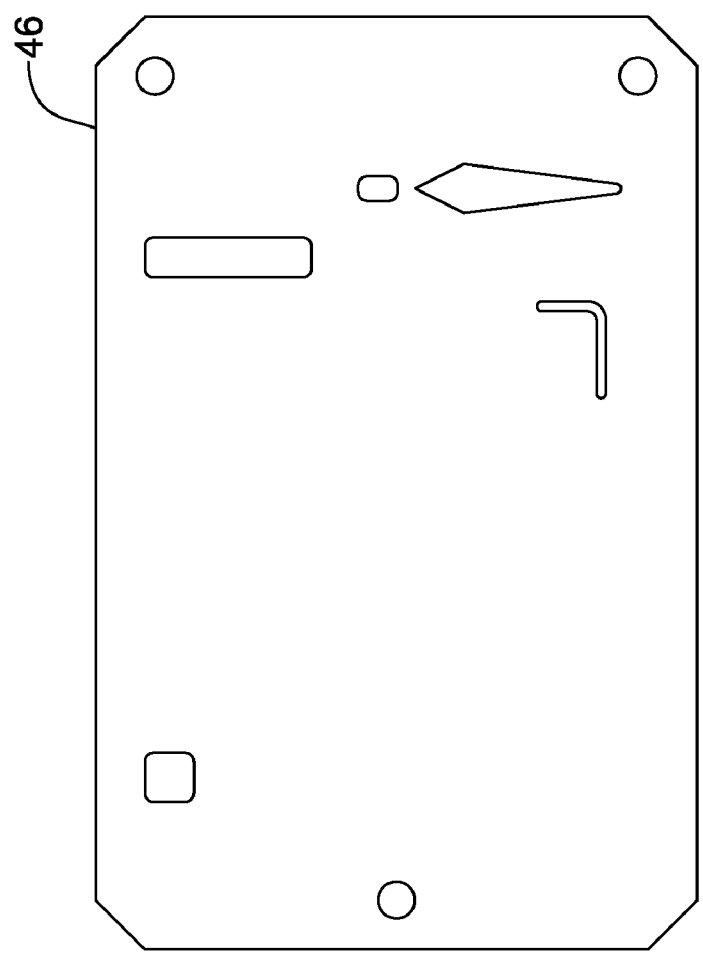
Figure 12:
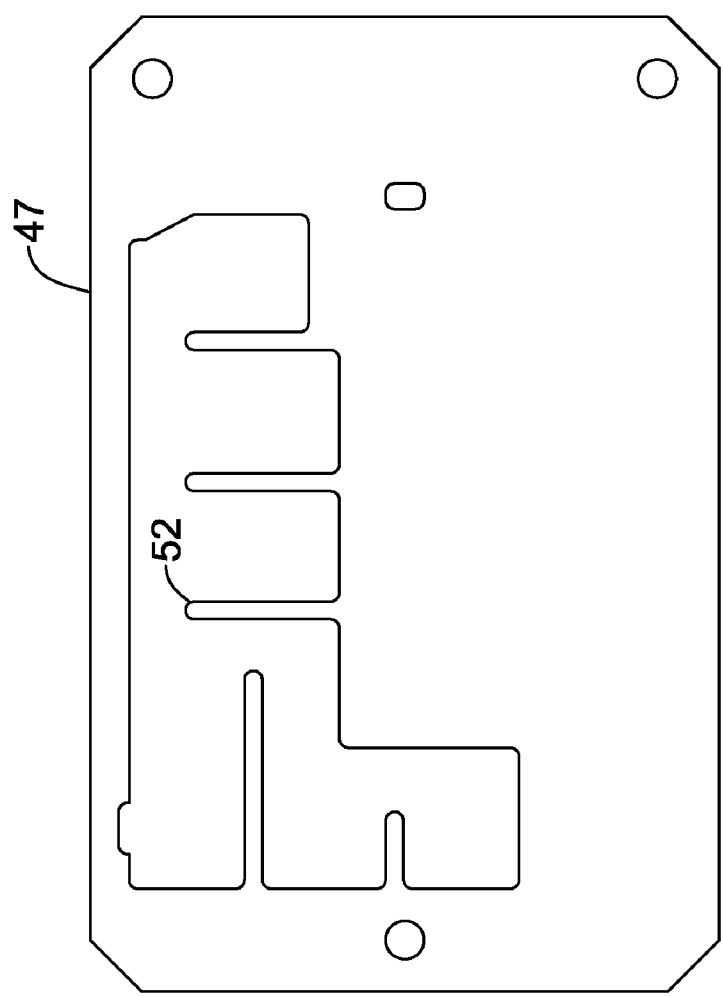

FIG. 4 shows a plan view of card 40 with layers stacked together, with certain fluidic circuit details having some dimensions in millimeters (mm). FIG. 5 shows layer 42 with some channel details. FIG. 6 shows details of some items on layer 42. FIG. 7 shows layer 43 along with some details. FIG. 8 shows layer 44 with details, including an anti-settling loop 51. FIG. 9 shows several items in some detail, including loop 51 of card 44. FIGS. 10 and 11 show layers 45 and 46, respectively. FIG. 12 shows layer 47, including some ribbing 52 of a waste chamber.

Many of the components of the microfluidic circuit may be long and narrow channels with volumes and cross-sections (width and height) as indicated in the tables in FIGS. 20 and 21. The height dimensions may be the smallest and have the tightest tolerances since they most affect pressure loss, sedimentation rate, and diffusion speed in the channels. The channel widths and lengths may often be nominal, but the volumes do need tolerances.

Figure 13:
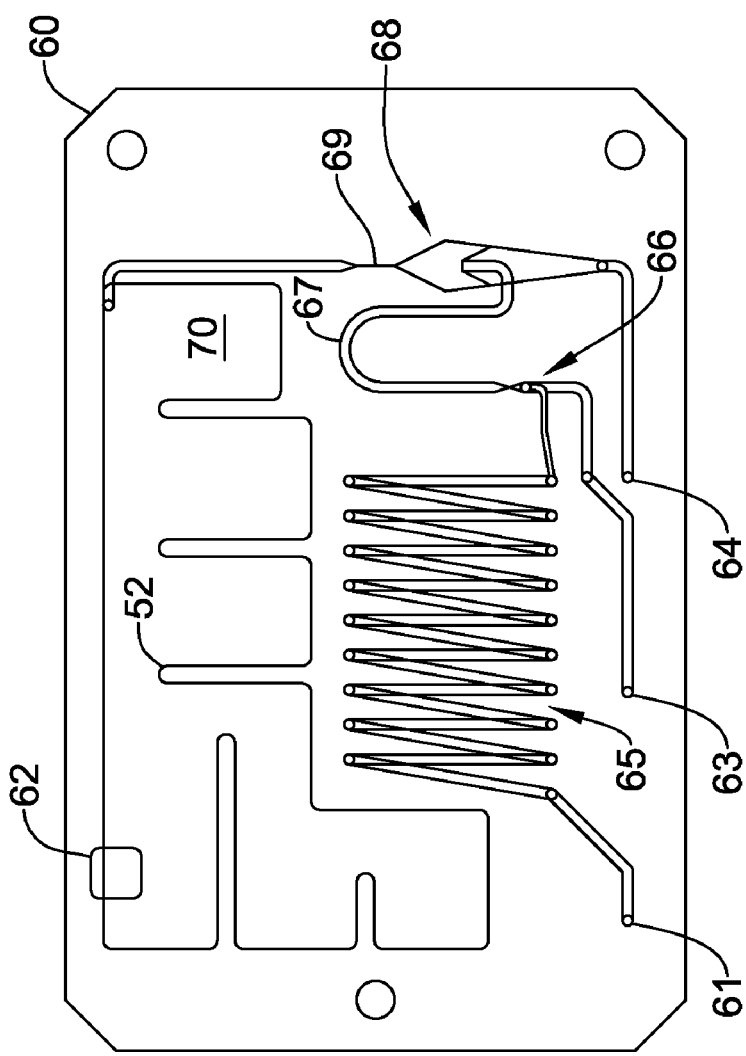
FIG. 13 shows a layout of components on the card.

FIG. 13 reveals key features of RBC cytometer card. The sample may be whole blood loaded into a sample loop 65 through a port 61. Sphering solution and sheath fluid (they could be the same fluid) may be pumped into the card through ports 63 and 64 respectively. These ports may be located to correspond to o-ring connections on the test manifolds. Port 61 may be sized to match a syringe needle tip used to load the blood sample. An improved interface may have needles on the manifold that penetrate elastomeric septums on the card 60. The base of these needles may press against the elastomer, providing a low-compliance seal during operation. After the assay, the septum may self-seal and prevent leakage while handling the card for disposal.

The vent hole 62 may prevent buildup of pressure in the waste tank as it is filled. It may have a porous membrane that allows passage of gas, but not liquid. The sample loop 65 may be a long and thin channel for several reasons. One may include system dynamics. The response (e.g., "pushback") of the sample flow to transient events in the large flows (i.e., sphering solution and sheath fluid) may be reduced by increasing the flow resistance and inductance and by reducing compliance of the sample loop channel. Another may include sample uniformity. The sample pusher fluid may very likely cleanly sweep the sample from the sample loop 65. If the sample loop 65 were a short wide channel, the pusher fluid should sweep through the channel center leaving much sample blood behind along the walls.

There may be an injection-molded version of the sample/diluent injector. The physical shape of the plastic film laminate version may be different, but its operation appears the same. Blood may be ejected from a hole in the trailing edge of a three-layer laminate into a faster flowing surrounding stream of diluent (sphering solution in the RBC card). This trailing edge may be shaped so that the blood is immediately flattened into a thin ribbon by the diluent flow. The sample/diluent injector channel may then narrow into an orifice so that the fluid velocity is increased sufficiently to sweep out air bubbles that might get trapped as the fluid channel thins from five layers to one. The sample/diluent injector 66 may be oriented to place its outlet on top so that during priming its buoyancy will encourage trapped air to leave.

The sphering channel 67 may be roughly an upside-down U shape that has wide vertical legs to provide residence time for the sphering reaction and has narrow horizontal legs to minimize cell sedimentation, which would adversely impact cell count accuracy.

The focusing chamber 68 may be analogous in form and function to the sample/diluent injector 66. The diluted sample is ejected from the trailing edge into the 5-layer deep body of the focusing chamber 68. The trailing edge may be shaped so that more of the surrounding sheath fluid approaches the ejected stream from the sides and compresses it into a narrow stream. Hydrodynamic focusing may continue as the sides of the focusing chamber 68 converge as the optical channel 69 is approached. As in the sample/diluent injector, the ceiling and floor of the focusing chamber may switch from 5 layers deep to 1 just before the optical channel so that the fluid velocity is high enough there to sweep out bubbles that may become trapped in that region. The focusing chamber 68 may be oriented so that buoyancy effects will help remove trapped air during priming.

The optical channel 69 may be as narrow and thin as possible with the laminate technology and optical sensors in use. The fluid optical channel 69 height may be set by the thickness (100 microns) of two-sided tape comprised of a 50 micron PET carrier film with a layer of 3M-501FL adhesive (25 microns) on each side. The optical channel 69 width (200 microns) may be set by the narrowest laser cut than can be produced by a ULS™ laser machine. If the decision is made to switch from green filter material to clear for layers 3-5, then the optical channel 69 width may be increased to 300 microns to prevent reflections from the channel wall of the optical sensor illumination. The optical channel 69 length may be made as short as possible if it is the dominant flow restriction and if the corresponding pressure rise in the card adversely impacts system dynamics. Molding technology may provide other perspectives of fabrication of optical channel and other analyzer card structures.

The waste tank 70 may be sized to hold the volume of all fluids injected into the card 60. It may have ribs 52 to minimize compliance so that it does not operate as a bellows displacing fluids while the card 60 is manually handled. Its inlet may be designed so that the entering fluid does not form drops which introduce temporal variability in the fluid flows rates, but that it instead wicks down through an open-sided channel to the bottom of the tank.

The card may have stiff outer layers to eliminate as much compliance in the card as possible. Less compliance means higher fidelity of internal fluid flow rates to the external driving fluid flow rates, i.e., higher fidelity=better control.

Figure 14:
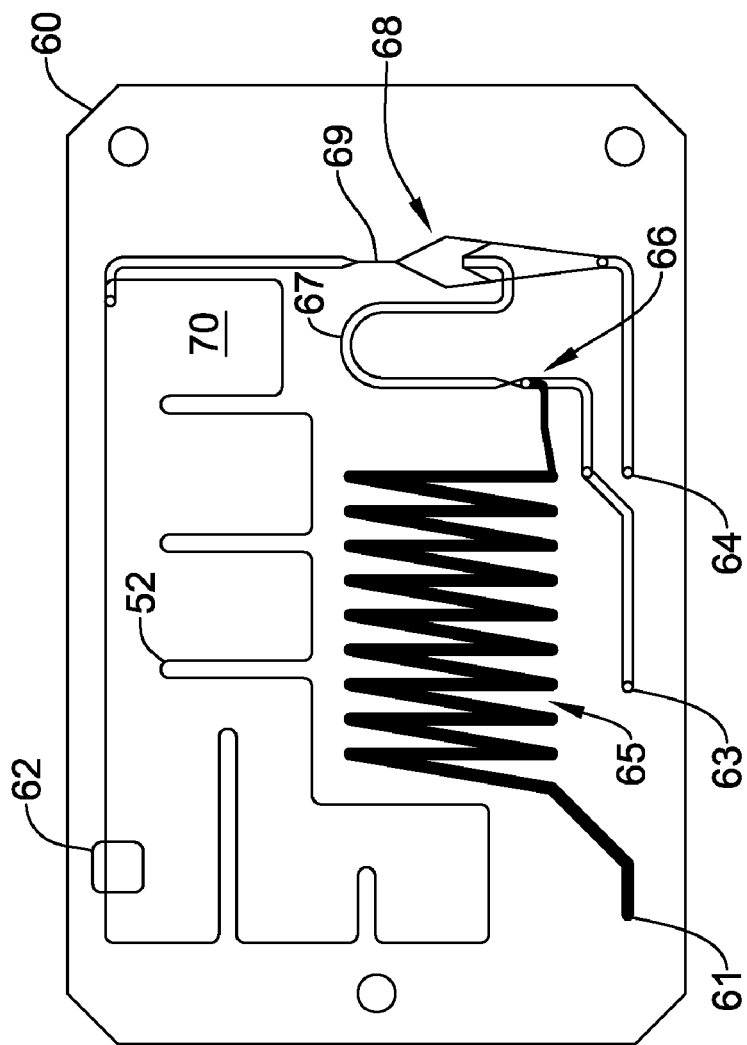
FIGS. 14-18 indicate fluid movements for a red blood cell analysis on a card.
Figure 15:
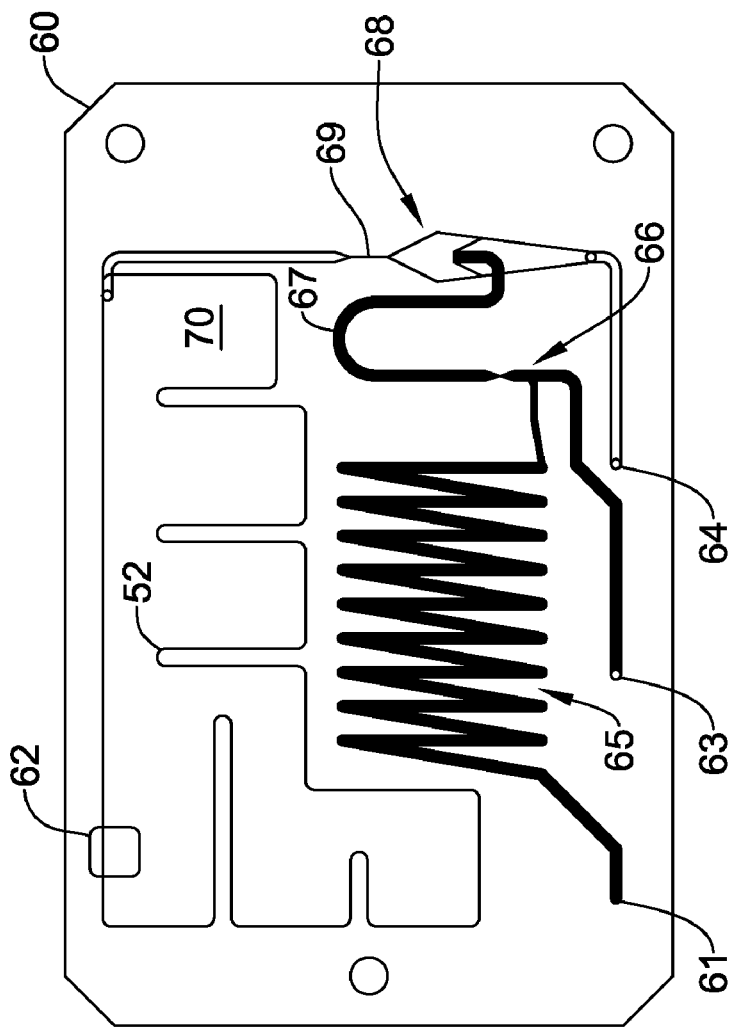
Figure 16:
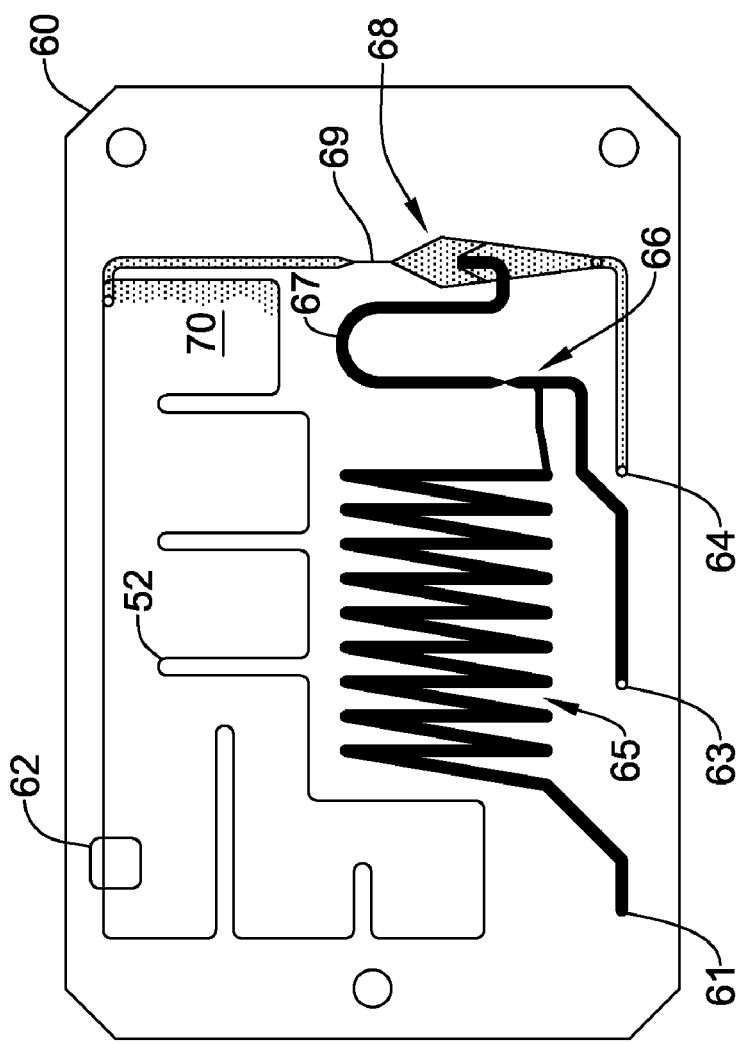

Flow rates and timing, and a set-up process may be noted. One may preload whole blood at 61 as shown in FIG. 14. Then the card 60 may be into a manifold. One may wet out the sphering channel 67 with sphering solution as shown in FIG. 15. The one may wet out focusing chamber 68, optical channel 69, and waste tank 70 as shown in FIG. 16.

Figure 17:
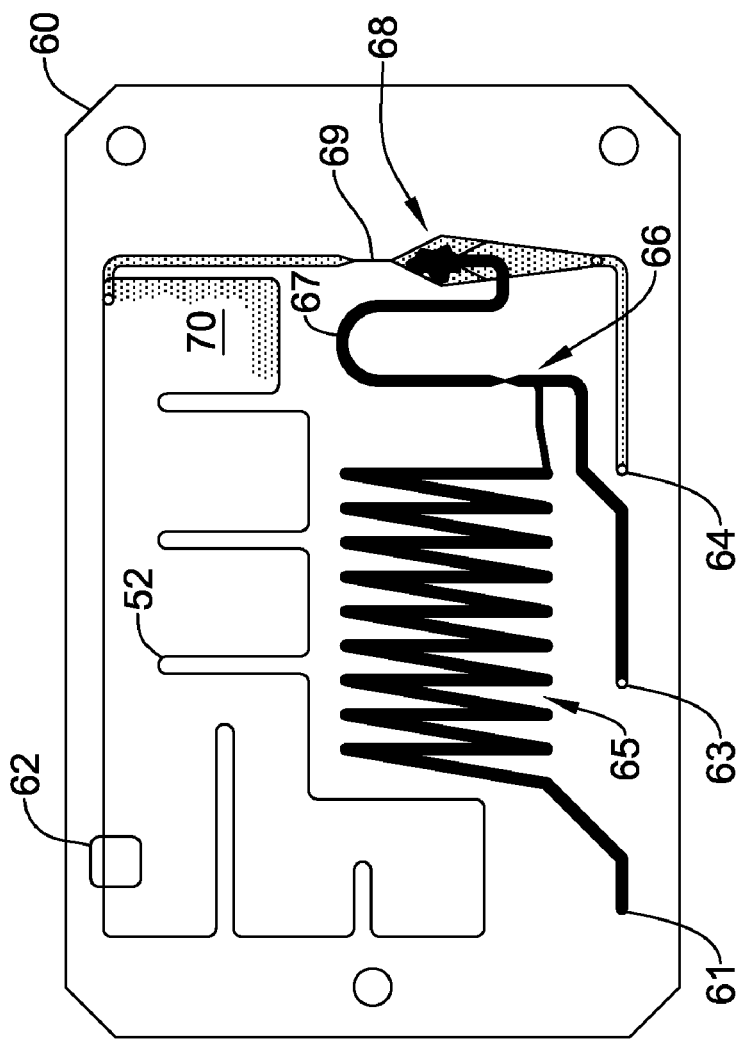
Figure 18:
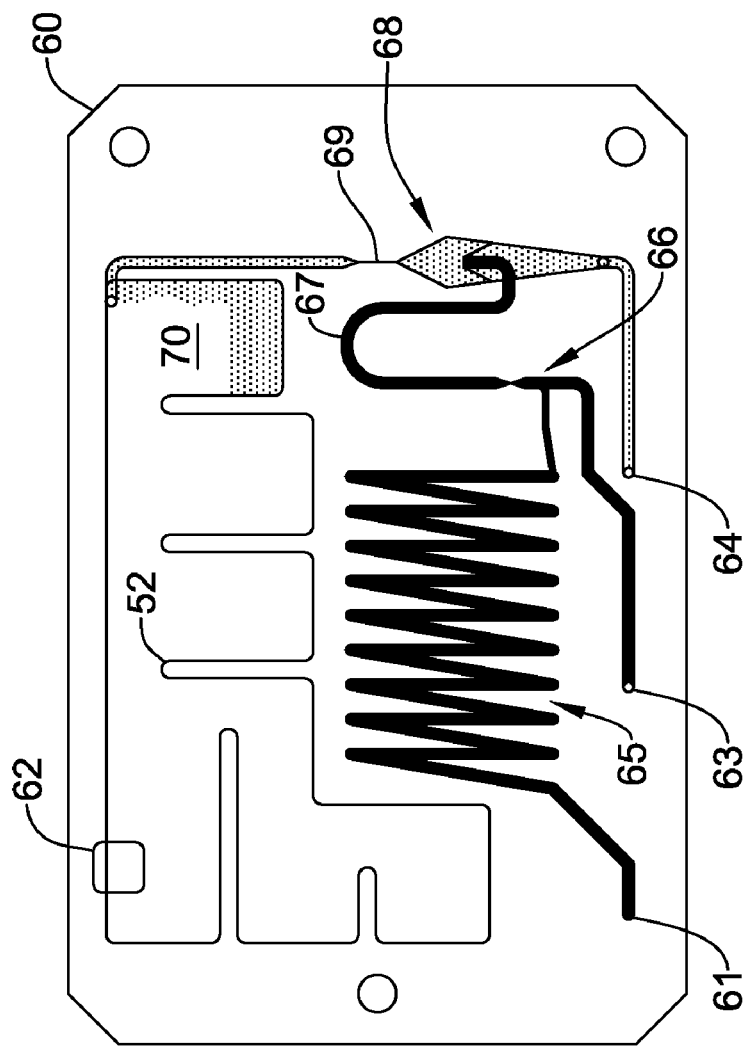

A two-step cycle may begin at t=0 sec. While continuously pushing sample with pusher fluid (a) at 1.5 µl/min, the sphering loop may be charged with a sphering agent to port 63 at 450 µl/min to obtain correct dilution of whole blood, duration=10 sec, as shown in FIG. 17. The sheath fluid at port 64 may flow at 450 µl/min, and cells may be counted, with a duration=60 sec, as shown in FIG. 18. The two-step cycle may be repeated until sample is exhausted or waste tank 70 is full.

Volume tolerances may be noted. The components that store fluids should have specific tolerances. The whole blood storage loop 65 may have a nominal volume of 16 microliters with a tolerance between 15 and 18 microliters. The dilution channel may have a nominal volume of 3 microliters with a tolerance between 2.75 and 3.3 microliters. The waste tank 70 may have a nominal volume of 3000 microliters and tolerance between 2900 and 3600 microliters.

Channel width tolerances may be noted. The width of several channels shown in FIG. 19 may be critical and require specific tolerances. The roughness tolerance on channel walls may be 0.010 mm (0.0004 inch). Various dimensions may be noted. Optical channel 69 may have a nominal dimension 71 of 0.2 millimeter with a tolerance of +/−0.010 millimeter. The channel focusing chamber 68 may have a nominal dimension 72 of 0.2 millimeter with a tolerance of +/−0.010 millimeter. Dimension 73 at the sphering channel 67 entry may have a nominal dimension of 0.2 millimeter with a tolerance of +/−0.010 millimeter. Sample/diluent injector 66 may have a nominal dimension 74 of 0.39 millimeters with a tolerance of +/−0.015 millimeter. A nominal dimension 75 may be 1.3 millimeters with a tolerance of +/−0.050 millimeter.

Layer thickness tolerances may be noted. There may be channel features that have relatively large compliance and introduce system dynamics problems. These areas include the sample loop, the focusing chamber, and the waste tank. Much of this compliance problem may be rectified by use of thicker material for layers 41 and 47. A table in FIG. 20 lists the materials and desired thickness tolerances of each layer of the card. They may be based on requirements for fluidic and optic performance. Some of these listed tolerances may be tighter than the general layer thickness tolerances generally utilized for RBC cards. This is because general thickness tolerances may be larger than those typically encountered during microfabrication. For example, some materials, such as PMMA, have a relatively large thickness variation from sheet to sheet as purchased from suppliers. However, the thickness variation over a particular sheet may generally be much less. A particular lot of cards made from a particular sheet should exhibit this reduced variation. The layer thickness tolerances in the table of FIG. 20 may be regarded as superceding and be used in quality control procedures.

Surface energy should be uniform throughout the channels to be wetted. An overall value of between 40 and 60 dynes/cm may be appropriate for a card in general, but the uniformity of surface energy of a particular card should be limited to a few dynes/cm. This may be demonstrated by a bubble-free wetout of the channels in which the wetting velocity is nearly constant over each constant channel cross-section. Channel wetting should not exhibit pauses followed by wetting velocity surges leaving air bubbles trapped behind the fluid front.

Quality control should include the following metrics for the fabricated cards. Each card should meet tolerances on key dimensions of card design. The thickness of combined layers 43-45 should be 0.008 inch+/−0.00023 inch (from the root sum of the squares of the percent tolerances) for consistent dimensions in optical channel. Uniform surface properties in channels may be verified by bubble-free wetout of random sample cards in each manufacturing lot. The channels of the cards should be free of dust particles larger than 1 micron, hair, and the like. The purpose is to avoid channel blockage and avoid the interference of foreign bodies during cell counting. There should be sufficient adhesion of adhesive layers such that pressurization of card channels of 10 psi gage does not cause leakage of fluid between card layers.

There may be several RBC sampling alternatives. One may have a complete blood count (CBC) card based on a microscale flow cytometer including on-the-fly lysis of erythrocytes, two-step hydrodynamic focusing, and a pneumatic fluid driver system. The optic/electronic sampling frequency used with the cytometer may be sufficiently fast to accommodate the frequency at which white blood cells (WBCs) arrive in the measurement channel. There may be three orders-of-magnitude more red blood cells (RBCs) than WBCs in the same volume of blood. Since the whole blood sample flow rate cannot be slowed enough to reduce the cell arrival frequency to the current optic/electronic sampling frequency, one of several alternative RBC sampling strategies may be used.

A faster optic/electronic sampling frequency may be used. The arrival frequency $f_{arrival}$ of cells in the measurement channel may be the product of the number density $\rho_N$ of the cell (i.e., the number of cells per volume of sample) and the sample flow rate $Q_{sample}$, $$f_{arrival} = \rho_N Q_{sample}. \tag{1}$$

For accurate dispensing of sample, which is crucial to overall measurement accuracy, the design flow rate for the sample may be set at $Q_{sample} \geq 3$ μl/min=0.05 μl/sec. The number density of RBCs in normal whole blood may be $\rho_N$=5,000,000 cells/μl. Thus, the minimum requirement for sampling frequency may be $$f_{sampling} = f_{arrival} = 5,000,000 \cdot 0.05 = 250,000 \text{ Hz}.$$

This is over 83 times faster than a current sampling frequency of 3,000 Hz. Although the sampling frequency can be increased, an increase of two orders-of-magnitude may ordinarily be difficult to achieve. In addition, cell coincidence may be very high unless the VCSEL illumination length (nominally 20 μm) is reduced by two orders-of-magnitude as well.

There may be a serial operation which is to sphere and then count. One strategy to disconnect the minimum sample flow rate requirement from the maximum sampling frequency may be to operate in a serial batch mode. In this approach, the sphering solution and blood sample may be mixed diffusively and directed to a storage tank. After valves are switched to change the flow path, the sphered RBC solution may be pumped to the usual injection port of the focusing chamber. This strategy may accommodate serial dilution in which the required dilution is performed in two or more separate steps.

Valves and an additional flow sensor may add to the CBC card. Second, RBCs may have a specific gravity of approximately s.g.=1.1 and will tend to settle out in a storage tank. Using the mean cell diameter of RBCs in normal whole blood as d=5.5 μm=0.0055 mm, the kinematic viscosity of the sphering solution as ν=1 mm²/sec (i.e., the same as water), and the acceleration of gravity as g=9810 mm/sec², the settling velocity of RBCs in the sphered RBC solution may be $$v_{settling} = 2/9(d/2)^2(s.g.-1)g/v = 0.00165 \text{ mm/s or } 99 \text{ μm/min}.$$

If the sphered RBC solution is pumped from the bottom or the top of the intermediate storage tank, RBC sedimentation may have the potential to alter the cell count. The impact may be reduced by minimizing the stopped flow time $\Delta t_{stopped}$ between storing the sphered RBC solution and pumping it on to the measurement channel, ensuring that the vertical dimension of the tank is relatively large compared to the sediment height $y_{settling}$, the product of the stopped flow time and the sedimentation velocity, $y_{settling} = \Delta t_{stopped} v_{settling}$, and pumping the solution from an outlet in the storage tank that is above $y_{settling}$.

One may divert most of the sphered RBC to the waste tank. Instead of using the serial process strategy, a continuous-flow process may be utilized that separates the sphered RBC solution into two streams. One stream would be dumped directly to the waste tank, the second stream would flow to the measurement channel as usual. A flow sensor may be needed on the second stream to assure the correct amount of sample was being measured. As pointed out in serial process strategy, to match the current sampling rate, the sampled stream of the sphered RBC solution would be ⅟₈₃$^{rd}$, or 1.2 percent, of the total stream. Thus, over 98 percent of the sphered RBC would be diverted to waste, which appears to be a rather inefficient use of on-card storage. Control of the process may be achieved actively by varying the sample and diluent pumps to attain the correct flow rate for the sampled stream of the sphered RBC solution or attained passively by stopping the cell count when an appropriate volume of solution has been sampled, assuming that a maximum flow rate is not exceeded.

Another approach may include using a two-stage push of the sphered RBC solution into the measurement channel. The first stage (stage 1) may be a co-flow of the whole blood sample and the sphering solution with flow rates $Q_{sample}$ and $Q_{diluent}$ set to achieve both the minimum sample flow rate and the correct dilution. The sphered RBC solution may begin to fill the long sphering channel that leads to the focusing chamber and measurement channel. But before the solution reaches the focusing chamber and sampling starts, the second stage may begin by simultaneously stopping the sample flow and slowing the diluent flow sufficiently that the desired cell arrival frequency is achieved. The flow of sphering solution alone may continue while the RBCs are counted.

The sphering channel may be filled with a sufficient volume of sphered RBC solution during the first stage in that it will not be exhausted during the slow push during the second stage (stage 2) while RBC counting is performed. A table in FIG. 21 shows the flow rates of the sample and sphering solution for various dilution ratios calculated from equation 1 ($f_{arrival}=\rho_N Q_{sample}$) and a dilution factor DF. A dilution equation may be $$Q_{diluent}=DF f_{arrival}/\rho_N$$

The table of FIG. 21 also shows the volume of sphered RBC solution stored in the sphering channel during the stage 1, assuming an RBC counting time of 10 seconds, which should produce 30,000 counts.

In actual practice, stage 1 may proceed for several seconds (e.g., 5 seconds), producing 25-250 μl of sphered RBC solution, depending on dilution factor. Some of this would be used up at the beginning of stage 2 while the diluent pump flow rate slows to its design flow rate for stage 2. At this time, the optics and detector would be ready to proceed with the count. After the count, the remainder of the sphered RBC solution may be purged to waste.

This strategy differs from the serial process of strategy 2 in that the flow is never stopped, so sedimentation is reduced, no additional flow sensor is needed, since the same sensor can be used to measure the diluent flow rate during both stages, and no on-card valves are needed to switch channels on and off.

The table of FIG. 21 shows the flow rates of the sample and sphering solution for a two-stage push of sphered RBC solution, accommodating both minimum sample flow rate of 3 μl/min and maximum sampling rate of 3,000 Hz. Also, it shows a minimum volume of sphered RBC solution needed for a 10 second assay producing 30,000 counts. The stage 1 flows are shown to be very high at the higher dilution factors.

Several items in this approach or strategy may include the following. The flow sensor for the sphering solution may need to accurately measure flow rates that differ by two orders-of-magnitude between stage 1 and stage 2. This may be achievable even though the flow sensors are nonlinear over this large range, because they may be calibrated for these conditions. Changing the sphering solution flow rate by two orders-of-magnitude may be difficult to control due to capacitances in the fluidic system. A high sphering solution flow rate (i.e., over 4 times the typical sheath flow rate) may be required at the highest dilution factor. To reduce the sphering solution flow rate, a lower dilution factor (e.g., DF=100) could be utilized, but this may then require a correspondingly higher sheath flow to limit cell coincidence.

Figure 22:
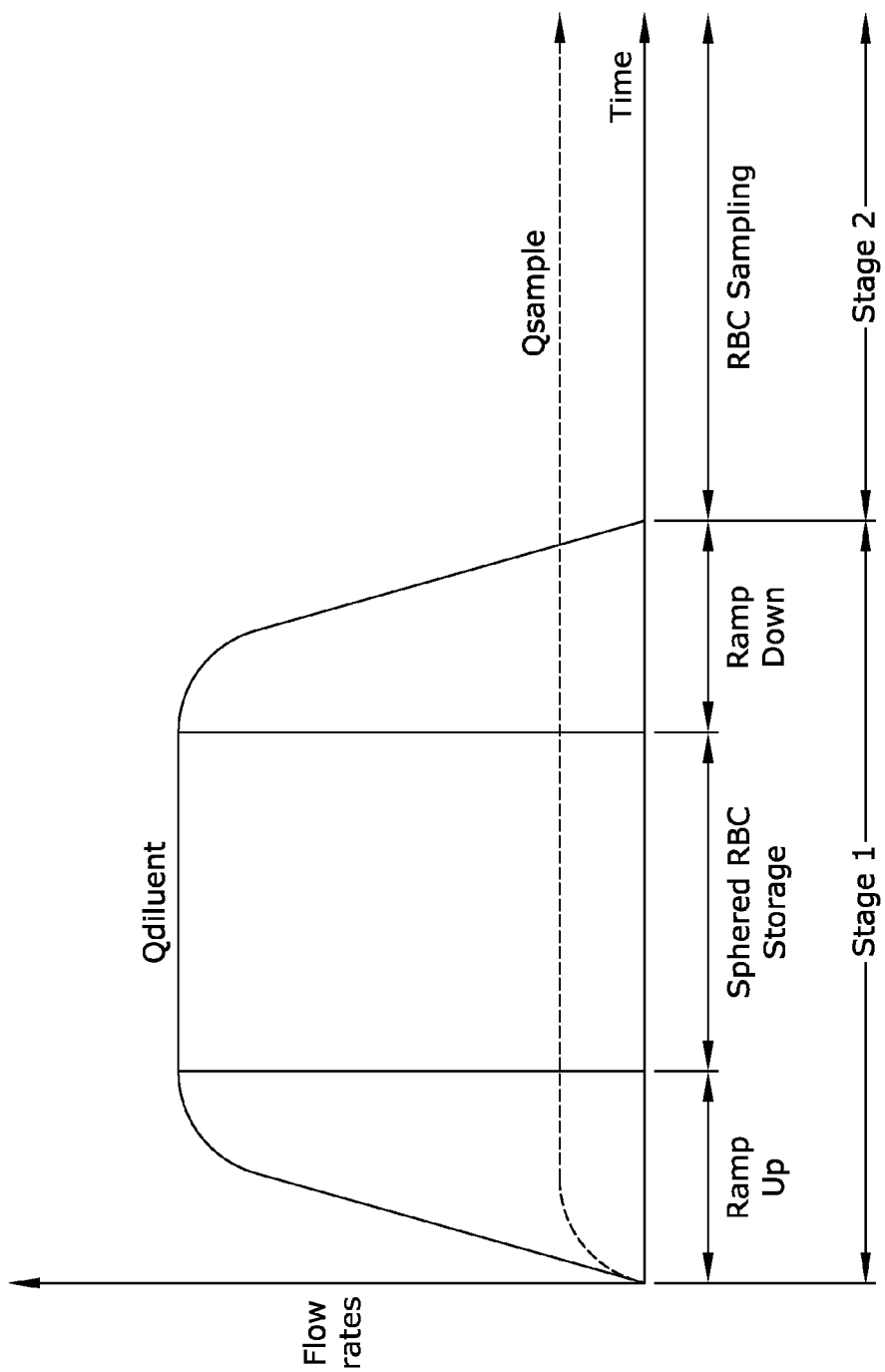
FIG. 22 is a graph of a control pattern for the sample and diluent pumps.

There may be a two-stage push of sphered RBC with continuous sample pumping. A variation in the previous strategy may be to utilize the sample pump to push the sphered RBC solution during the second stage push, instead of using the diluent pump. This may simplify the control dynamics since the sample pump could operate at a constant flow rate during both first and second stages. The diluent pump would only need to reach and hold one flow rate during the first stage and then slow and stop at the beginning of the second stage while the sheath pump starts up. A graph in FIG. 22 illustrates a control scheme or pattern for sample and diluent pumps during a two-stage push of sphered RBC solution for RBC sampling. Solution stored during ramp up may be discarded through the measurement channel during ramp down before RBC sampling begins. The volume of the sphered RBC storage needs to be sufficient for the RBC sampling period since the following fluid will tend toward whole blood.

The table in FIG. 23 shows a sphering solution flow rate and cell coincidence for a two-stage push of sphered RBC solution, assuming a sample flow rate of 3 μl/min, a sheath flow rate of 500 μl/min, and a sampling rate of 3,000 Hz. Also, the table shows the minimum volume of sphered RBC solution needed for a 10 second assay producing 30,000 counts. The stage 1 flows appear very high at the higher dilution factors. The table shows an impact of dilution ratio on the required diluent flow rate and the resulting cell coincidence.

Several points may be noted. Since it might not have the desired dilution, the sphered RBC solution stored during the ramp up period may be discarded through the measurement channel during the ramp down period before RBC sampling began. This may be facilitated by ensuring that equal volumes of fluid are moved by the diluent pump during the ramp up and ramp down periods.

The volume of sphered RBC solution accumulated in the channel between the sample injector and the focusing chamber (sphered RBC storage) needs to be sufficient to supply the entire RBC sampling period since the following fluid in the channel may become less and less dilute and tend toward whole blood.

The diluent flow rates appear high and may result in significant back pressure to the pump because of the restriction of the narrow diffusive-mixing channel downstream of the sample injector. This restriction may be significantly reduced by redesign of its geometry by shortening the length over which it is narrow and retaining its thinness in the z-direction. One may note that during stage 1 there would be no pressure loss through the measurement channel, since no fluid would have yet reached it.

Diluent flow rates could be reduced proportionately with the sample flow rate. For example, the rates could be halved if the sample flow rate was reduced to 1.5 μl/min.

The sheath flow rate may be increased from 400 to 500 μl/min without significantly increasing back pressure at the pump during the RBC sampling period in stage 2 because the diluent pump is off during that time.

There may be a high back pressure due to the combined diluent and sheath flow through the measurement channel during the ramp down period (as the sheath pump starts up) that may be destabilizing to the dynamic system. The sheath flow rate can be ramped up during the diluent's ramp down period so that the sum of the sheath and diluent flow rates is nearly constant over the ramp down and RBC sampling periods.

Figure 24:
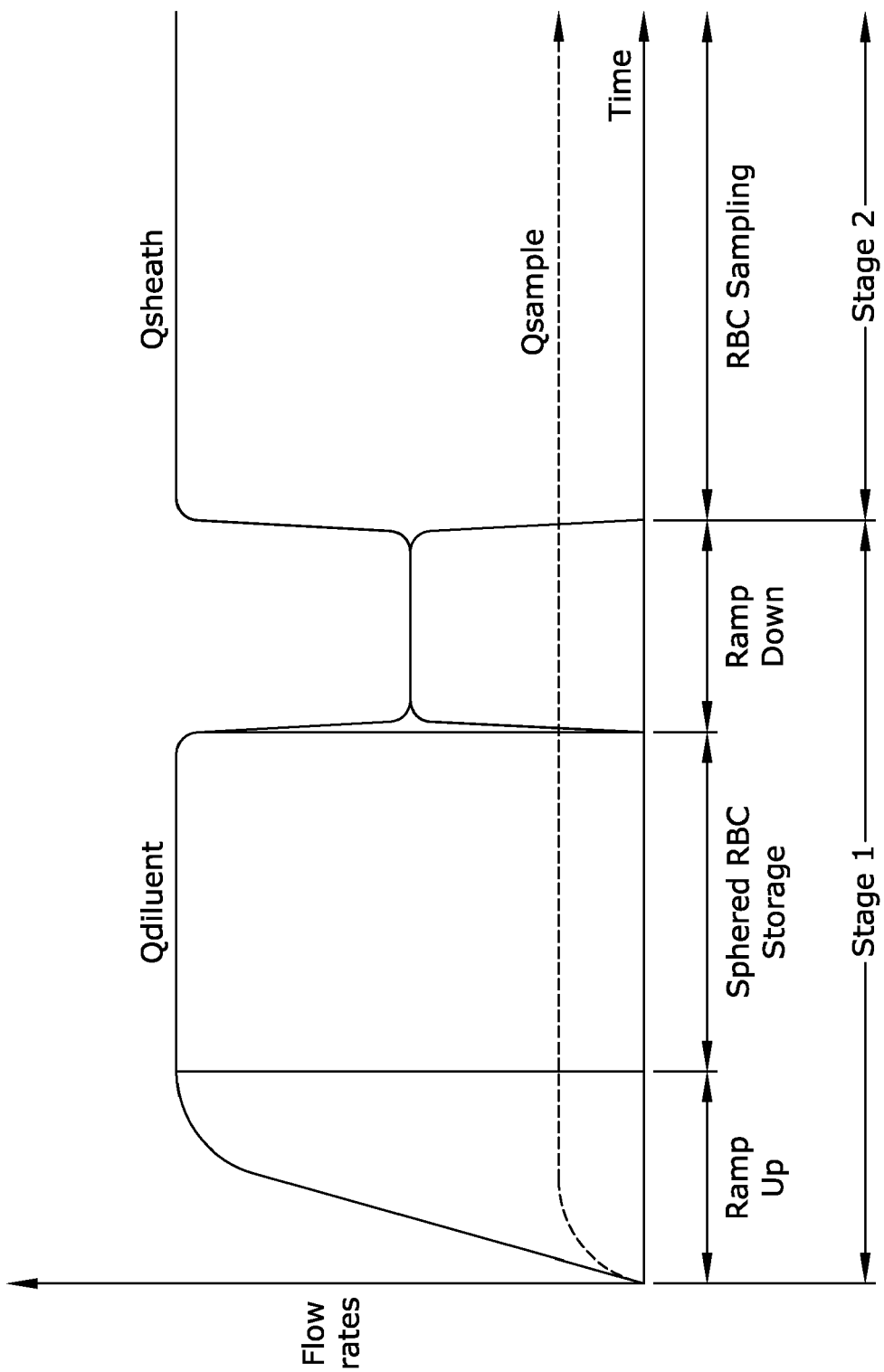
FIG. 24 is a graph of a control pattern for sample and diluent pumps during a two-stage push of sphered RBC solution for RBC samples.

There may be a two-stage push of sphered RBC with continuous sample pumping with equal flow rates of diluent and sheath. If one considers the possibility that the sheath solution may be the same as the sphering solution, it becomes possible to use the same pump to deliver both, sequentially, using valving to switch between pushing diluent and pushing sheath. FIG. 24 illustrates this case when one valve is opened, after the sphered RBC solution has been stored, to allow flow into the focusing chamber, then a second valve is closed that stops flow into the sphered RBC storage channel.

FIG. 24 shows a control scheme for sample and diluent pumps during two-stage push of sphered RBC solution for RBC sampling. The diluent pump is also used to push diluent used as sheath fluid. On-card valves switch the flow between channels. A solution stored during ramp up would be discarded through the measurement channel during ramp down before RBC sampling begins. The volume of the sphered RBC storage needs be sufficient for the RBC sampling period since the following fluid will tend toward whole blood.

A table in FIG. 25 shows the tradeoffs between diluent and sample flow rates, sampling time for the required number of counts, and the volume of storage needed for sphered RBC solution. In the cases shown, the resulting core should be 9 by 9 microns or, if manipulated by the geometry of the focusing chamber, 25 by 3 microns, i.e., very thin in the z-direction.

The table of FIG. 25 shows the sphering solution flow rate and cell coincidence for a two-stage push of sphered RBC solution, assuming a sampling rate of 3,000 Hz. One may note that the amount of sphered RBC solution required during sampling is typically less than 1.5 µl for these operating conditions.

The strategy 5, the two-stage push of sphered RBC solution with constant sample flow rate, appears appealing, since it does not require addition pumps, valves, or flow sensors, and yet meets the requirements of whole blood sample flow rate $Q_{sample} \geq 3$ µl/min and counting frequency $f_{sampling} \leq 3,000$ Hz. Potential challenges include maintaining dynamic control of the system with the large diluent flow rates utilized in the stage 1 push.

Strategy 6, which is a variant of strategy 5, allows the same pump (and flow sensor) to sequentially push sphering solution, first as diluent, then later as sheath fluid using valving to make the switch between flow channels. One may suggest moving forward with one of the operating conditions listed in table of FIG. 25.

An approach here may include determining if flow control can be maintained by the sphering solution pump when valves are operated to switch between using the flow to create sphered RBC solution and using it as sheath fluid. Then there may be determining how quickly the flow from the diluent pump can be ramped down from 100 percent to 50 percent of its maximum flow rate. This time may be compared to the time required to ramp up the flow rate from the sheath pump from 0 percent to 100 percent of its maximum value. The diffusive mixing channel downstream of the sample injector may be redesigned to reduce pressure loss in this fluid path. The platelet sampling process may be analyzed to determine how it could fit within the strategy 6 and whether platelet coincidence would be manageable.

A purpose of the sphering channel on an RBC cytometry card may be the exposure of red blood cells in a thin ribbon of whole blood to a sphering agent with sufficient residence time so that the sphering process is complete. The thin ribbon shape may be desirable because it permits the sphering agent to rapidly diffuse to erythrocytes and initiate their sphering. However, as soon as whole blood is diluted, its erythrocytes are not necessarily held longer in position by plasma proteins and begin to settle. The sphering channel may be designed to minimize sedimentation of erythrocytes, a significant source of cell count error.

Figure 19:
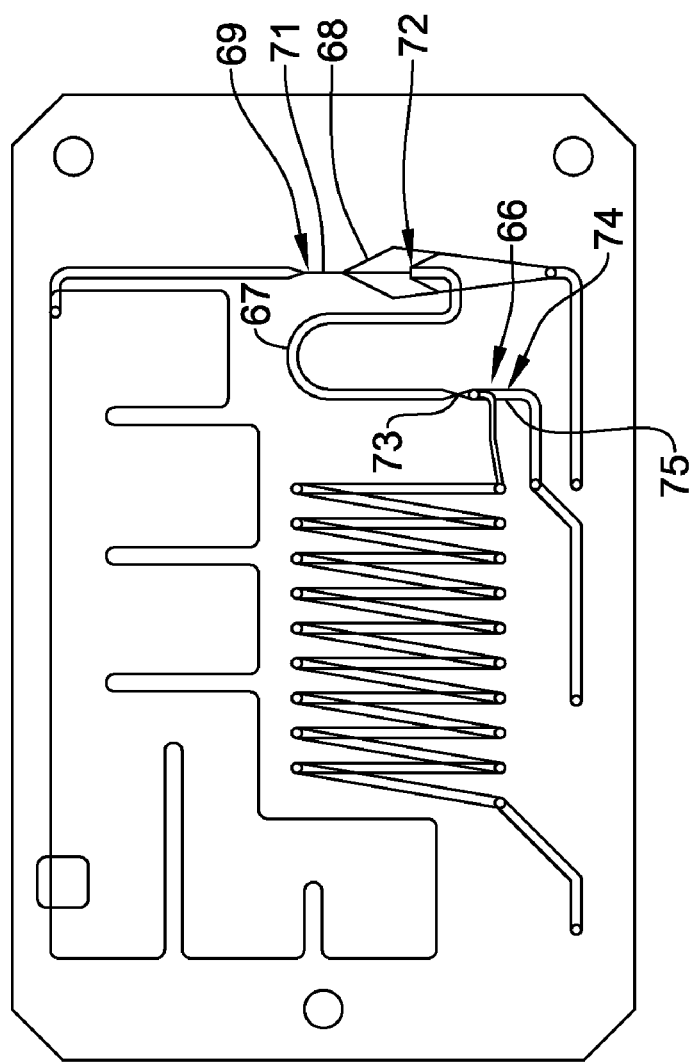
FIG. 19 indicates locations of some of the critical measurement tolerances.
Figure 26:
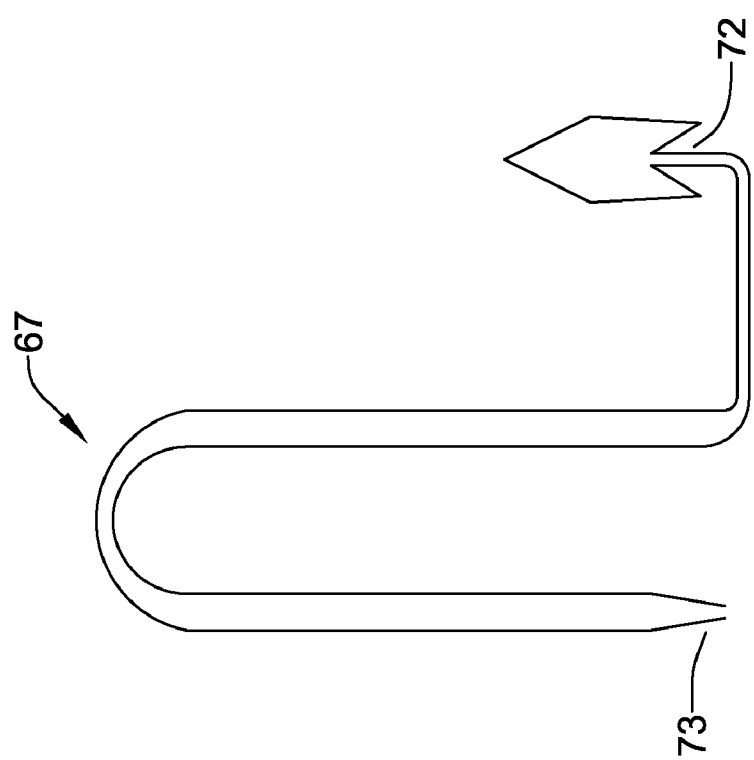
FIG. 26 is an illustration of a red blood cell sphering channel.
Figure 27:
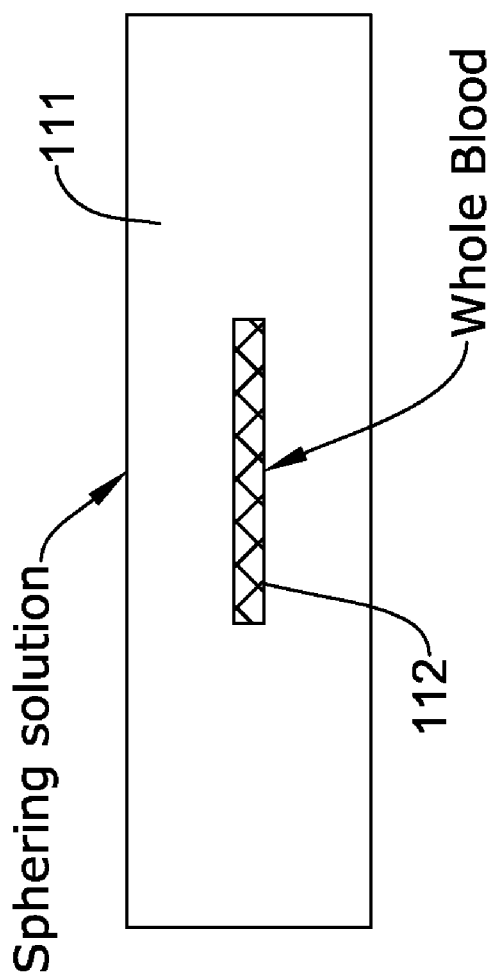
FIG. 27 shows a cross-section of blood in a channel of sphering solution.

The sphering channel may be one of the fluidic channels of the RBC cytometry card. An RBC card is shown in FIG. 19. The sphering channel 67 is the curvy section between the dimensions 73 and 72. FIG. 26 is a parametric sketch of the sphering channel 67. A thin ribbon 112 of whole blood surrounded by sphering solution 111 (FIG. 27) may enter the inlet on the lower left it 73 and flows to the outlet in the focusing chamber at 72. The view in FIG. 27 is looking downstream into the sphering channel. The cells are assumed to form a thin ribbon 112 at the center occupying 4.8 percent of the cross-section. FIG. 26 of the sphering channel shows parameter values which may be r1=2.5, m=0.2, n=0.4, and w=1.3, all in millimeters.

The residence time of the erythrocytes (cells) in the sphering channel need to be long enough for the sphering agent to completely sphere them. But since the cells are denser (due to their iron content (hemoglobin)) than the surrounding aqueous solution, the cells may be settling every moment, so residence time should be kept to the minimum as necessary. In a horizontal channel, there is by its nature very little distance to the wall where cell sedimentation can occur. Cells that arrive in near-wall regions where the flow velocity is low are likely to form a sediment and are unlikely to become re-entrained in the flow. In a vertical channel, cell settling may reduce cell number density in a rising flow and increases number density in a falling flow. In laminar flow around a corner, the higher velocity is near the inner radius. The outer radius flow tends to be much slower. These considerations lead to the following items. Horizontal channels may be made narrow to increase the local flow velocity and reduce cell residence time there. The vertical channels may be made wide to slow the flow and provide most of the cell residence time in the sphering channel. It may be ensured that the vertical channels are ascending and descending channels of equal length to minimize variation in cell number density. One should smoothly narrow the channel around corners so that regions of slow flow where cells might collect are avoided.

Initial conditions may include the following items. At the beginning of the simulation, the sphering channel may be filled with pure sphering solution. There should be no cells present and the fluid flow velocity should be zero. In reality, the sphering channel may initially be filled with air, so there may be an approach for wetting the channel.

Boundary conditions at the inlet of the sphering channel may implement a load-dispense cycle of the sphering channel. The input flow rate may vary over time and the cell number density may vary spatially over the input flow cross-section. The concentration profile of cells may include a thin ribbon of cells are located at the center of the channel 67 inlet. The blood flow may be constant at 1.5 µl/min. It may be assumed that the sphering solution flow rate ramps up from zero to 450 µl/min during the first second, ramps back down to zero from 9.5 to 10 seconds, and then remains at zero for awhile. In essence, whole blood, initially sheathed by sphering solution, may enter the sphering channel 67 at its inlet and proceed to the focusing chamber. The outlet of the sphering channel may be maintained at zero pressure (relative to atmospheric pressure).

The momentum transfer between blood and sphering solution may assume a Wallis (1969) model (initially developed to model a buoyant bubble in a water column) with bubble (cell) diameter of 5.5 µm. The density of the sphering solution may be $\rho=0.001$ gm/l and the dynamic viscosity is 0.001 Pa s. The specific gravity of the cells may be assumed as 1.11 and the specific viscosity as 5.5. The acceleration of gravity is regarded as 9810 mm/sec.

A model of the sphering channel may be developed using a numerical multiphysics approach. The computational approach may include modeling of fluid motion by conservation of mass and momentum. A computational mesh of finite volumes may be employed to model the essential features of the device geometry. The numerical approach employed may be a Two-Fluid method that models the motion of two fluids—blood cells and sphering solution— and the transfer of momentum between them. It may solve separate mass and momentum conservation equations for each fluid, which allows inclusion of the interactions between the body force on cells due to gravity and the interphase drag force. These equations are related by a volume fraction, Alpha, which is taken as the volume fraction of blood cells in each finite volume.

Calculation of the motion of each of the fluids as they proceed through the sphering channel may be accomplished by independent application of momentum conservation for each fluid. The Navier-Stokes equation may be used for an incompressible Newtonian fluid, which is a consequence of the application of Newton's second law to the fluid in the system. It is $$\frac{\partial \rho \alpha u}{\partial t} + u \cdot \nabla \rho \alpha u + \alpha \nabla P - \mu \alpha \nabla^2 u - F = 0$$

which is a general equation that may be used for complex three-dimensional flow fields with a vector velocity $u=(u_1, u_2, u_3)$, the volume fraction of blood cells $\alpha$, the pressure gradient $\Delta P$, the fluid density $\rho$, the fluid viscosity $\mu$, and a body force F that includes gravity force and interphase drag force. The equation may be solved independently to model each of the two fluids, which may then be related by an interphase momentum transfer relation in terms of the drag force between the cells and the sphering solution. A constant viscosity may be assumed for the blood cell phase, when in reality the viscosity may decrease as the sphering solution diffuses in and dilutes the blood sample stream.

Pushback of a sample in to the sample loop may be common in cytometer cards. Pushback may be caused by a sudden increase in pressure in the sample/diluent injector due a sudden starting of the diluent and/or sheath flow. the increase in pressure may cause reverse flow into any upstream compliance in the card structure or the fluid. Because the sample rate is so small, it may take many seconds for the sample to return to the injector, even though the pushback volume is less than a microliter.

In the RBC card, the sample pushback may be in response to the starting point of the diluent flow. Flow sensors located between the card and the syringe pumps have not yet shown any obvious reverse flow, so the compliance may be suspected to be in the sample loop. Since the card may be non-compliant or physically stiff, the sample fluid is suspect.

Figure 28A:
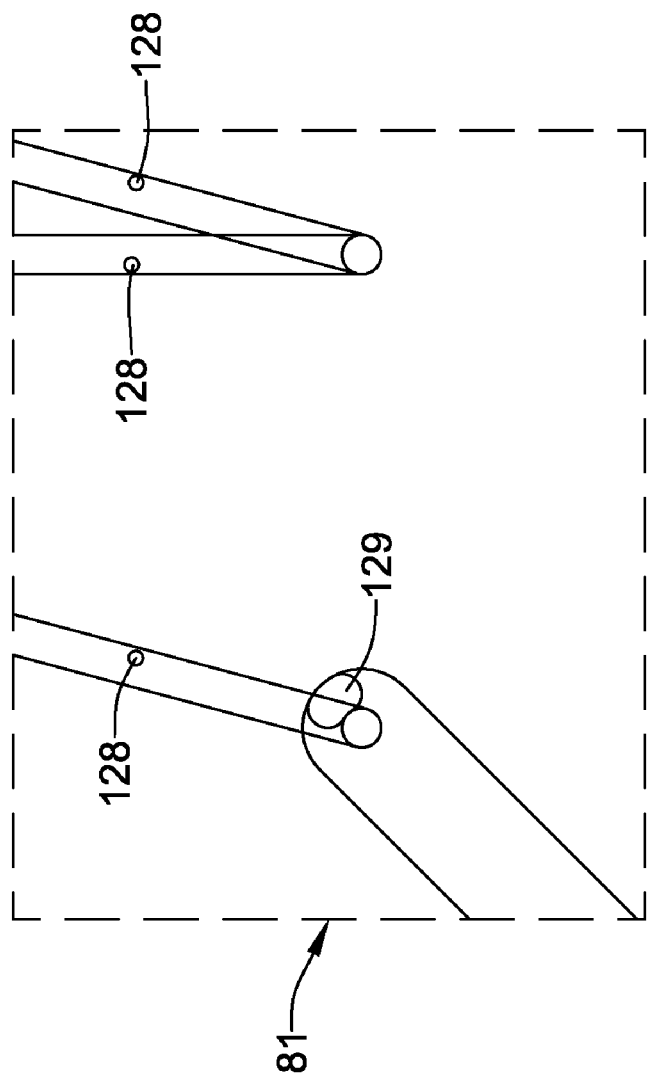
FIG. 28 shows various designs of channel and via interfaces for bubble reduction.
Figure 28B:
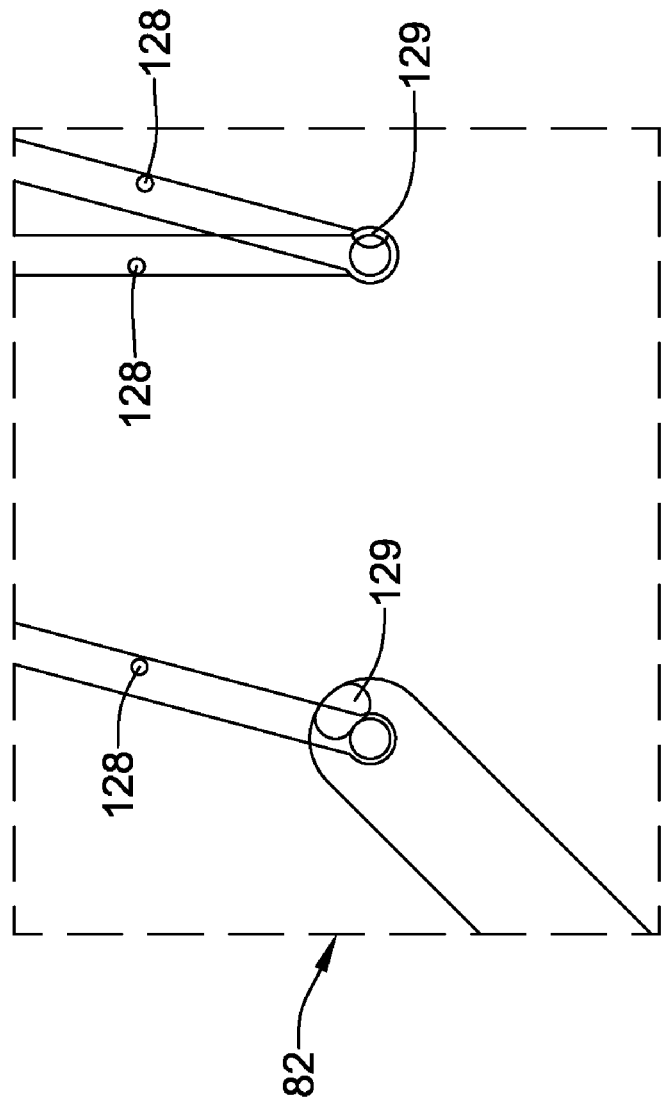
Figure 28C:
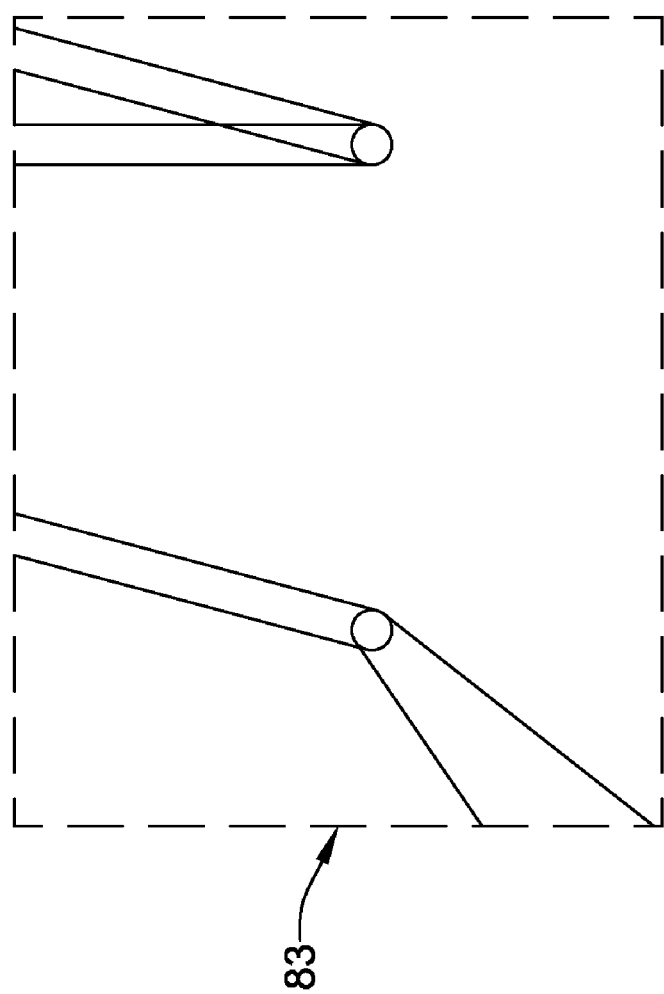

A sample fluid may be loaded into three cards, which are inspected for bubbles, a very likely source of compliance. Two cards may have designs 81 and 82 as illustrated in FIG. 28. These cards may have a variation in which the channel ends are expanded to be larger than the via between them. The cards may be loaded or filled manually at roughly two different flow rates. One rate may be fast, i.e., about 5 ul/sec. The other rate may be slow, i.e., about 0.2 ul/sec. In designs 81 and 82, approximately 25 micron diameter bubbles 128 may appear occasionally along the walls of the channel. Also, in designs 81 and 82, a large bubble 129 may occur in the wide entry channel located behind the via. A design 83 has channel ends that are the same size as the via between them. No bubbles should occur in design 83. With the fast fill, the proportion of vias containing air bubbles may be about 30 percent for design 83 and about 100 percent for designs 81 and 83. With a slow fill, the proportion of vias containing air bubbles may be about 0 percent for design 83 and about 50 percent for designs 81 and 82.

The tiny bubbles along the walls may be caused by wall roughness (not wall waviness), which could trap air during a filling. The walls of design 83 appeared smoother than the walls of designs 81 and 82 and thus exhibited fewer bubbles. Slow filling may minimize these bubbles.

Vias should be the same size as the channel ends. Small vias relative to the channel ends) correlate with bubble formation. The channel ends should not be bulbed out. The walls should be straight. Either the via diameters may be increased to match the channel ends, or the channel ends should be decreased to match the vias. The largest bubble generally appears at the end of the input channel. Such channel should be altered as shown in design 83 of FIG. 28 to eliminate the bubble trap.

FIGS. 29-34 show examples of components for particle settling solutions on RBC analysis cartridges. Such components may or may not be a part of or a replacement for sphering channel 21 of FIG. 1b, sphering channel 51 of FIGS. 4, 8 and 9, and sphering channel 67 of FIGS. 13-19. The components of FIGS. 29-34 have configurations that exhibit anti-settling or anti-accumulation properties for hindering particle setting, such as that of red blood cells. These components may be sphering channels.

Figure 29:
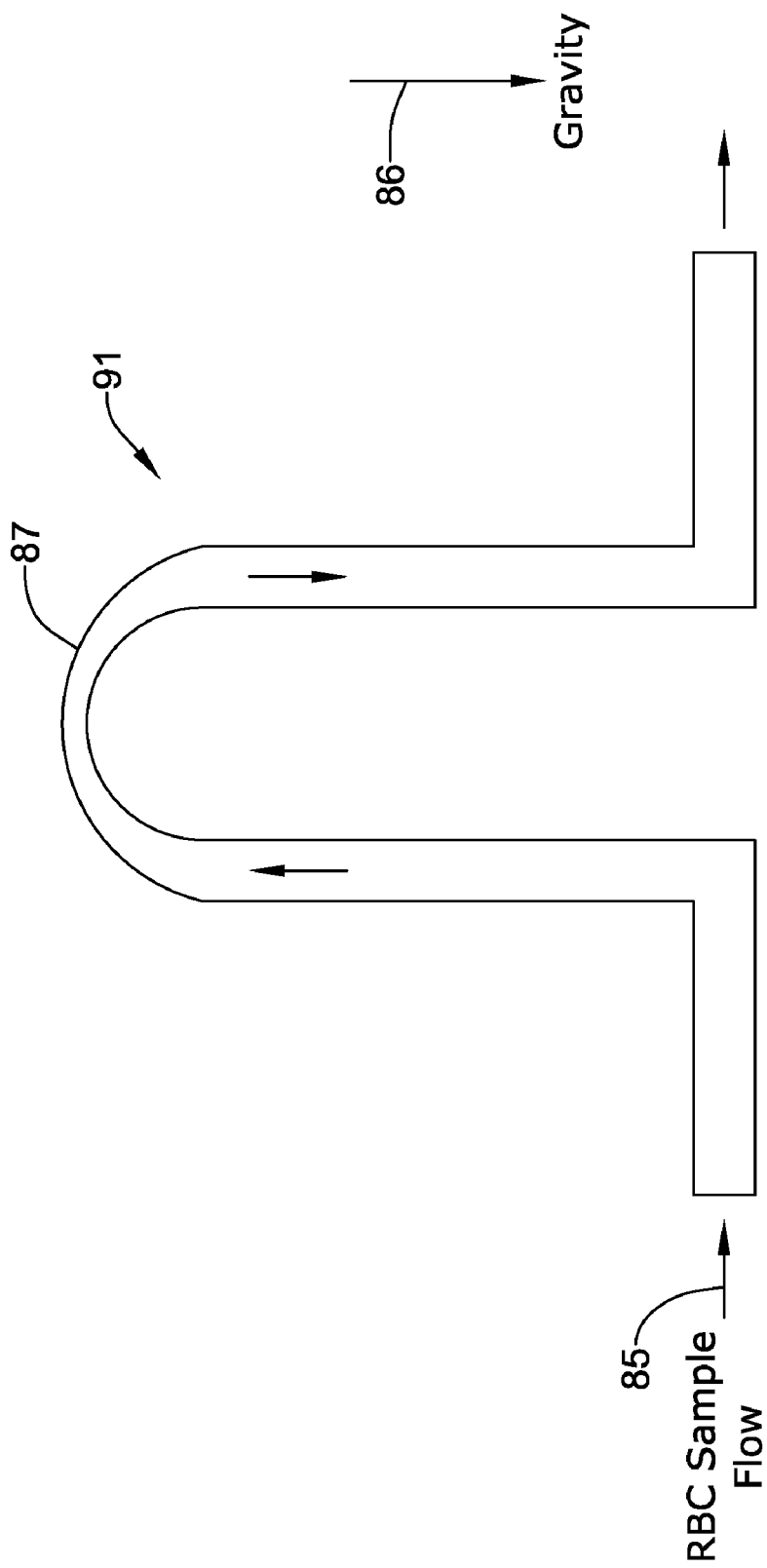
FIGS. 29-34 are various configurations of sphering channels having anti-sediment or anti-accumulation characteristics.

In FIG. 29, an RBC sample 85 may flow into device or channel 91. The flow may eventually flow upward approximately parallel but against the force 86 of gravity. As the flow approaches the top of the channel 91 it may go through a u-turn or curved portion 87 of channel 91 and return downward toward the exit of channel 91. The internal cross-section of channel 91 may become smaller or more constrained in the u-turn or curved portion 87. This, in conjunction with the gravity, may reduce or prevent an accumulation and non-movement of red cells to prevent settling of the red cells in the channel. The u-turn portion may be about 180 degrees, or may be regarded as being about between 90 and 270 degrees.

Figure 30:
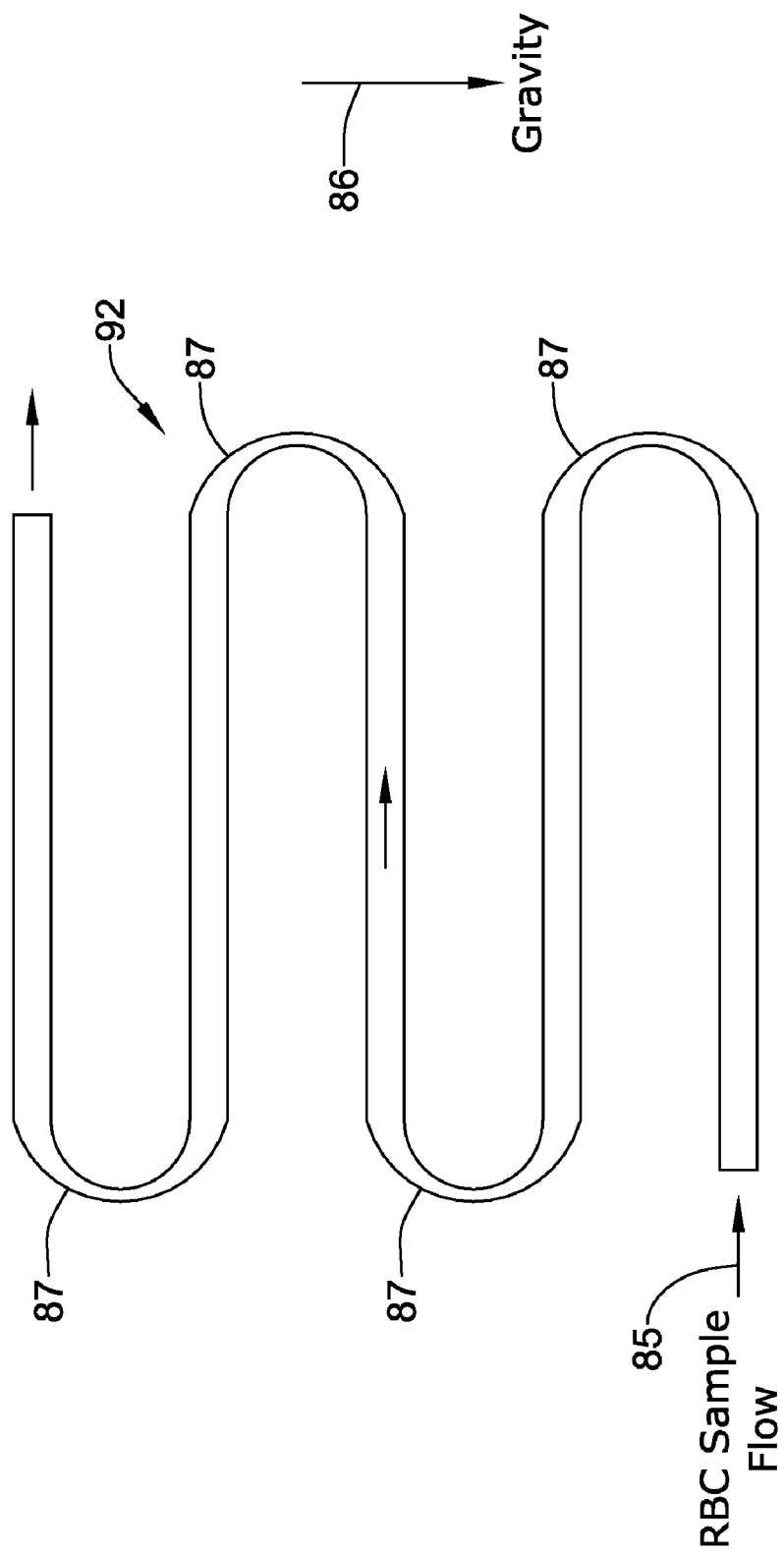

FIG. 30 shows a snake-like channel 92. The RBC sample flow may enter at the lower portion and turn up and go to the opposite direction at u-turn or curve 87 and move in a horizontal direction and turn again at curve 87 to move in the opposite direction. In the example channel 92, the flow may encounter four u-turns 87. There may be more or less turns or curves 87. The u-turns may typically be about 180 degrees, or may be regarded as being about between 90 and 270 degrees. The channel 92 may be positioned such that the upward movement of flow 85 is in the opposite direction of the gravity force 86. Channel 92 may reduce or prevent accumulation or collection of sediment or cells.

Figure 31:
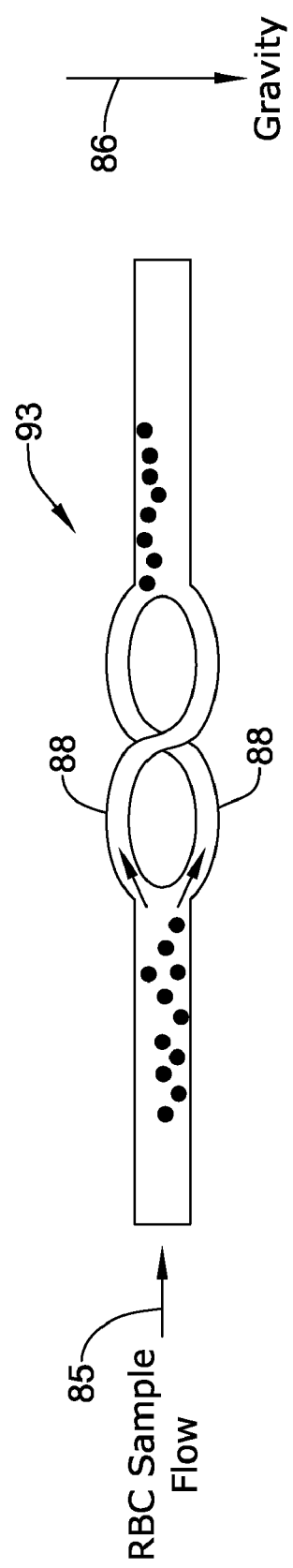

FIG. 31 shows another anti-settling or anti-sediment accumulating device 93. The RBC flow 85 may enter channel 93 in a horizontal direction. Channel 93 may split into two or more sub-channels 88. A bottom sub-channel may curve up and combine with the other sub-channel into a full channel. A top sub-channel may curve down and combine with the bottom sub-channel into the full channel. The overall direction of the flow 85 may be perpendicular to the direction of the gravity force 86. This configuration may be repeated in series.

Figure 32:
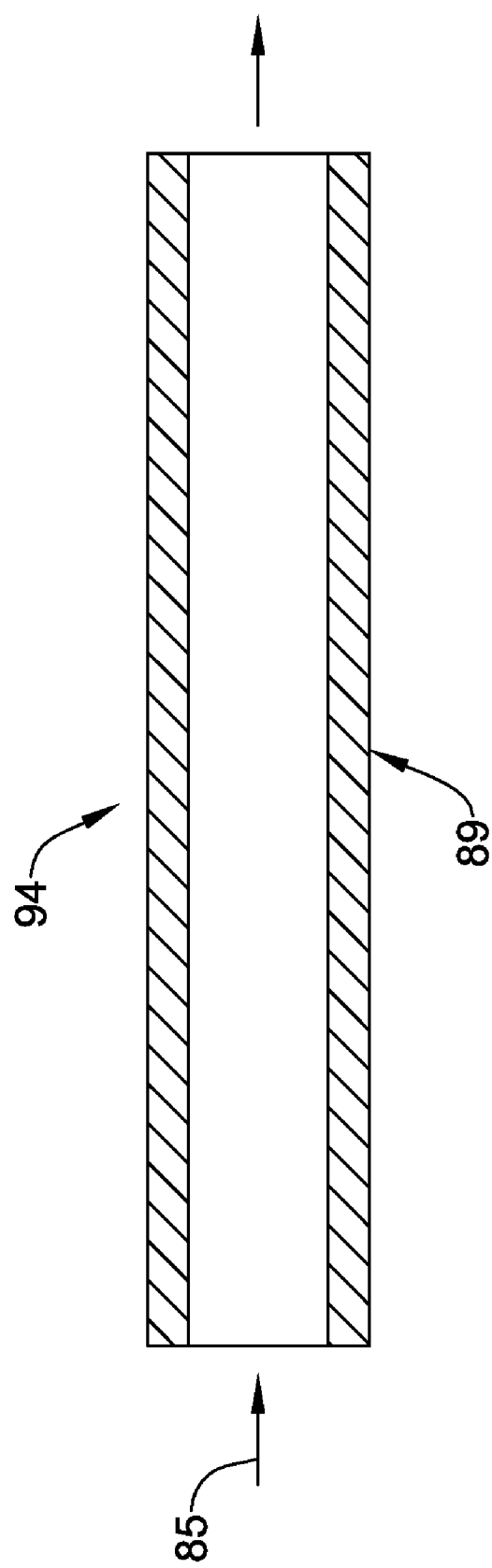

FIG. 32 shows a more or less straight channel 94 for an anti-settling or anti-sediment accumulating device. Also, the channel 94 might not be straight. An RBC sample flow 85 may enter and flow through the channel 94. Channel 94 may have a special inside surface which may be hydrophilic or hydrophobic. For instance, the surface may be hydrophilic to a fluid carrying the RBCs. Such fluid may be a diluent, sphering agent, lysing agent, sheathing agent, water, or the like. A hydrophilic surface may reduce the probability of blood cells or air bubbles attaching to the surface. Attached blood cells cannot be counted; attached bubbles can increase the compliance of the system and degrade the active control of fluid motion. However, many plastic materials that perform well in the plastic injection molding process are hydrophobic. In this case a pretreatment with, for example, a protein solution may cover the initially hydrophobic surface with bound proteins and thus create a hydrophilic surface.

Figure 33:
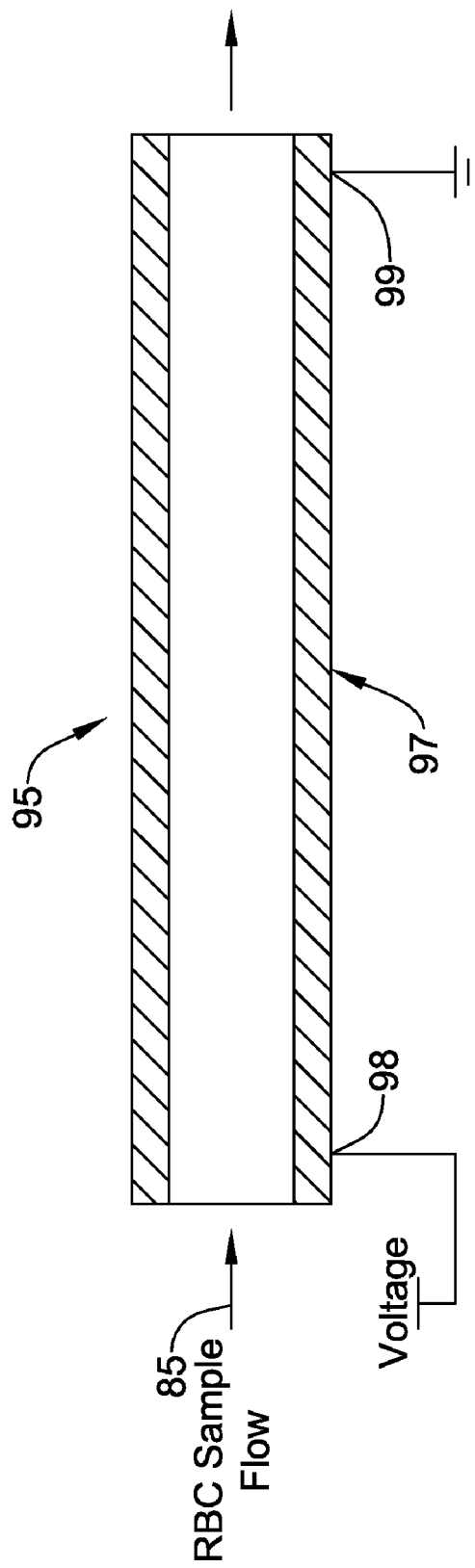

FIG. 33 shows a more or less straight channel 95 for an anti-settling or anti-sediment device. The channel might not be straight. An RBC sample flow 85 may enter and flow through the channel 94. Channel 94 may have an electro-wettable inside surface 97 where the surface energy changes with an applied potential. An electric potential or voltage source may be connected to the inside surface 97 near the entry 98 and of the channel 95 with a ground of the source connected to the surface 97 near the exit 99 end of the channel 95. An electric or voltage potential may be in the same manner but reversely in polarity to the surface 97 or in either polarity to certain portions of the surface 97.

Figure 34:
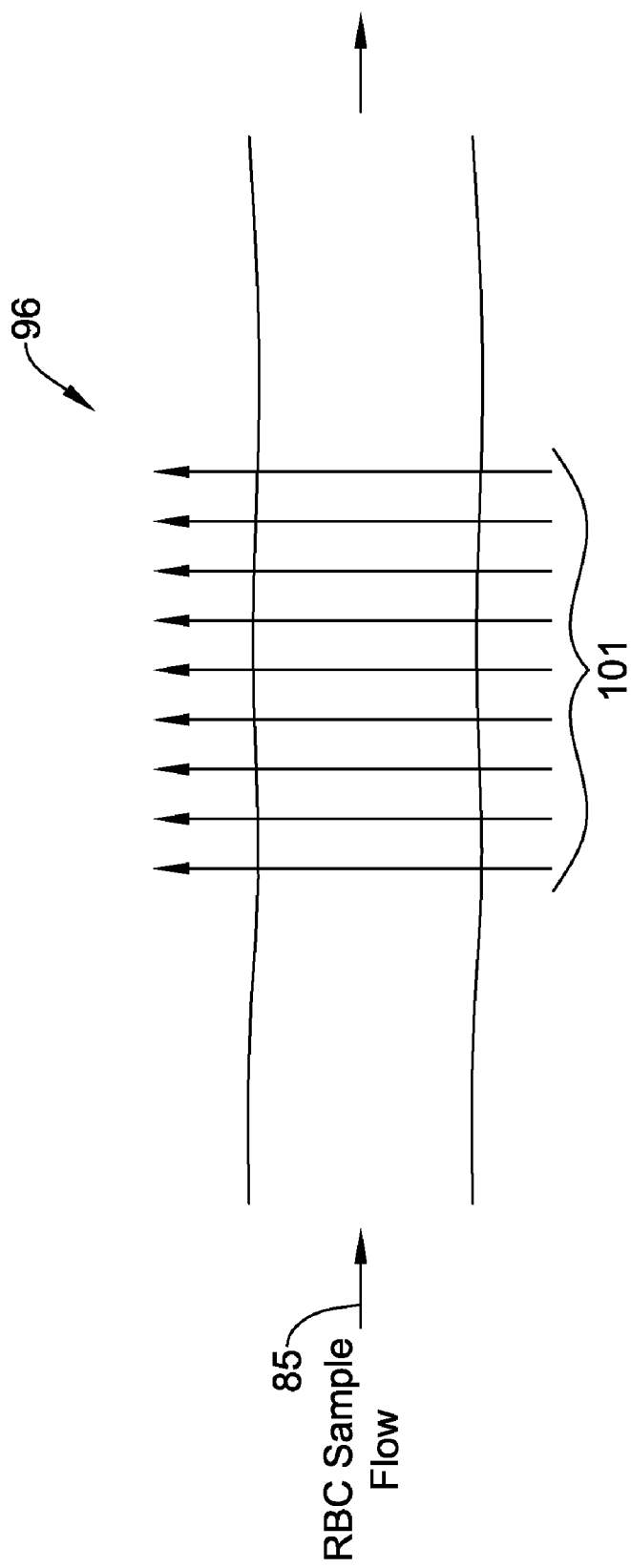

FIG. 34 shows a channel 96 designed for anti-settling of particles or anti-sediment accumulation. Channel 96 may be a straight or non-straight channel. An electric and/or magnetic field 101 may be applied through channel 96 approximately perpendicular to the sample flow 85 to effect anti-settling or anti-accumulation properties in the channel relative to at least red blood cells having iron.

Figure 35:
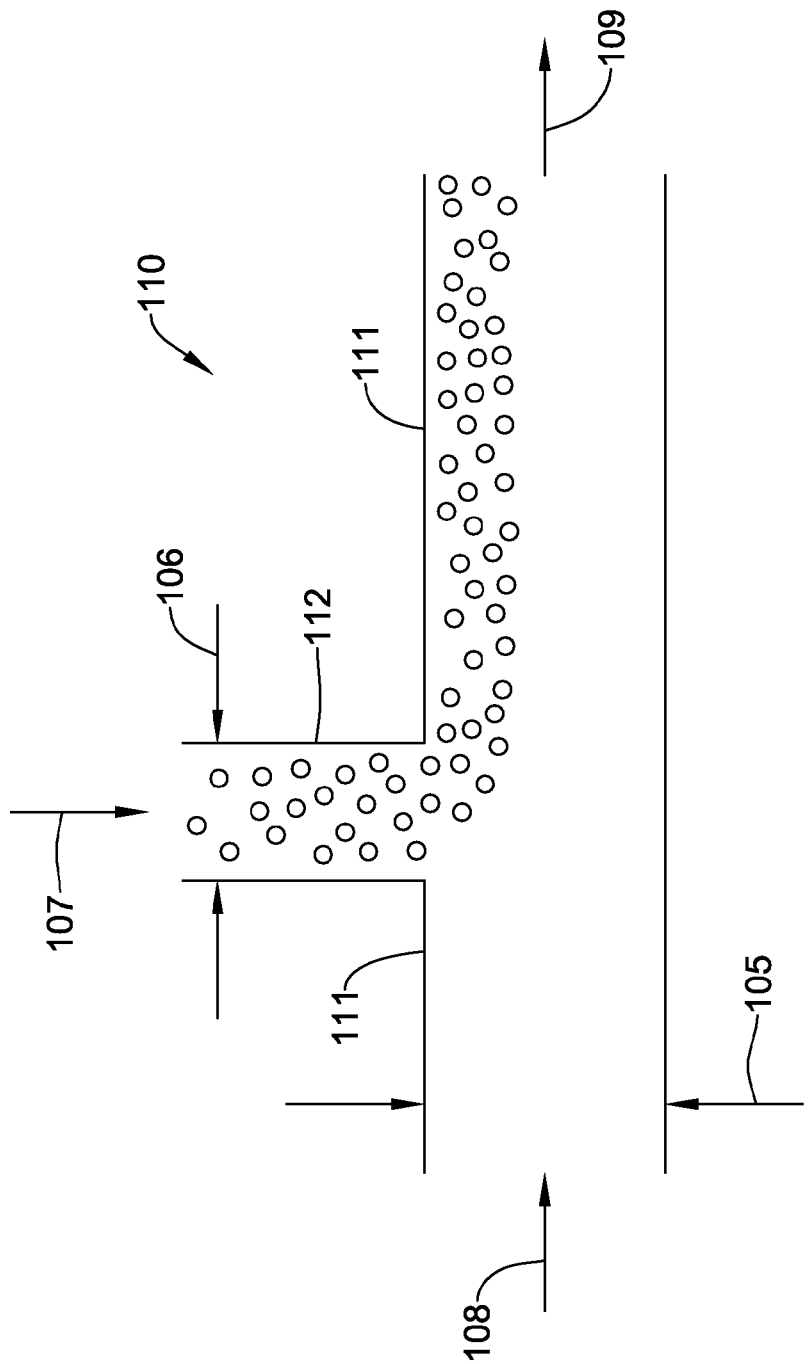
FIG. 35 shows a junction for minimizing a clumping of a sample.
Figure 36:
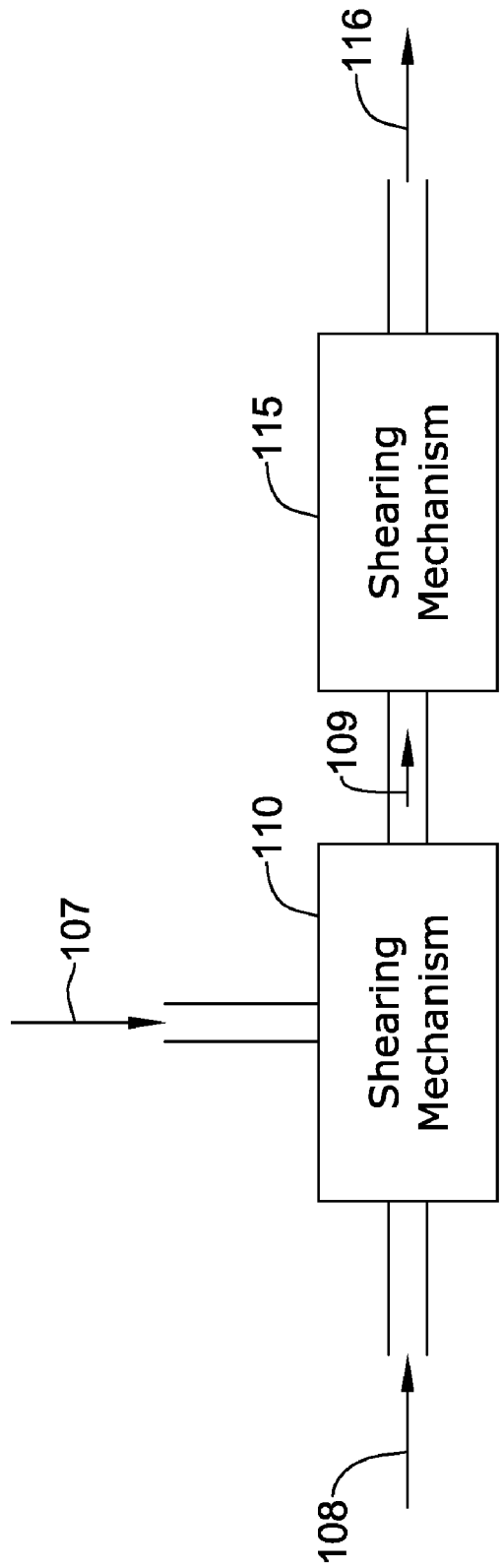
FIG. 36 is a block diagram of shearing and sphering mechanisms.

Since whole blood is a viscoelastic material, it can exhibit a clumping behavior as it is injected as a sample 107 into the lysing or sphering solution 108. One method to minimize this clumping behavior is shown in the T-junction configuration 110 of FIG. 35, in which channel widths 105 and 106 of channels 111 112, respectively, may be selected in conjunction with the sample 107 and reagent 108 flow rates to produce a shear of 1000 per second at the wall in the main channel 111 at the junction. This shear force overwhelms the viscoelastic restoring forces of the whole blood and minimizes the clumping behavior. Channel 112 may operate as an injector. The reagent 108 combined with sample 107 may flow downstream in the main channel 111 to the next stage of the microfluid network of the cartridge. The next stage may be a sphering channel or mechanism 115 which may be one of the versions described herein and illustrated in FIGS. 29-34, or mechanism 115 may be another version. FIG. 36 shows the shearing mechanism or configuration 110 in conjunction with the sphering mechanism 115 having a sphered sample output 116.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A fluidic analyzer system comprising:
a removable cartridge having a microfluidic circuit; and
a housing for holding the removable cartridge; and
wherein:
the microfluidic circuit is for at least partially providing a blood count of a sample; and
the microfluidic circuit comprises:
    a first structure for reducing sediment settling of the sample;
    a second structure for reducing clumping of the sample;
    a sphering mechanism connected to the second structure;
    a sheathing mechanism;
    a hydrodynamic focusing chamber connected to the sphering mechanism and the sheathing mechanism; and
    an optical channel connected to the hydrodynamic focusing chamber for at least partially achieving the blood count.

2. The system of claim 1, wherein the sphering mechanism is for providing a portion of blood to waste so as to maintain a continuous flow through the sphering mechanism to reduce sediment settling of the sample.

3. The system of claim 1, wherein the first structure is at least partially integrated with the sphering mechanism.

4. The system of claim 1, wherein the blood count comprises a red blood count, a platelet count, a mean cell volume determination of RBCs, multi-part differential counts of white blood cells (WBCs), and/or hemoglobin absorbence-based measurements.

5. The system of claim 1, wherein the second structure is for applying a shearing effect on the sample to nearly eliminate clumping of the sample.

6. The system of claim 1, wherein the second structure is a sample injector having a T-junction to a flow channel of the microfluidic circuit.

7. The system of claim 1, wherein channels of the first structure, second structure, sphering mechanism, and/or hydrodynamic focusing chamber, have connecting ends which are about the same size to reduce a presence of bubbles.

8. The system of claim 1, wherein the first structure comprises:
a channel having a continuous path that is approximately straight for a first distance, curved about between 90 and 270 degrees for a second distance and approximately straight for a third distance; and
wherein:
the channel is situated in a field of force having a first direction; and
the first distance and the third distance are approximately parallel to the first direction.

9. The system of claim 8, wherein:
the channel is a sphering channel; and
the field of force is a gravity force.

10. The system of claim 1, wherein the first structure comprises:
a channel; and
wherein:
the channel comprises:
    a first segment having an elongated dimension approximately perpendicular to a first direction;
    a second segment connected to the first segment, having an elongated dimension that curves about between 90 and 270 degrees; and
    a third segment connected to the second segment, having an elongated dimension approximately perpendicular to the first direction;

the channel is situated in a field of force;
the field of force has a force in the first direction; and
the second segment is situated in a plane approximately parallel to the first direction.

11. The system of claim 10, wherein the channel is a sphering channel.

12. The system of claim 1, wherein the first structure comprises:
a channel; and
wherein the channel comprises:
a first segment;
a second segment connected to the first segment;
a third segment connected to the first segment; and
a fourth segment connected to the second and third segments;
the second segment sequentially curves in a first direction and a second direction way;
the third segment sequentially curves the second direction and the first direction;
the channel is situated in a field of force; and
the channel has an elongated dimension approximately perpendicular to a direction of the field of force.

13. The system of claim 12, wherein:
the channel is a sphering channel: and
the field of force is a gravity field.

14. The system of claim 1, wherein the first structure comprises:
a channel; and
wherein the channel comprises:
an inside surface; and
wherein the inside surface is hydrophilic.

15. The system of claim 14, wherein the channel is a sphering channel.

16. The system of claim 1, wherein the first structure comprises:
a channel; and
wherein channel comprises:
an inside surface; and
wherein the inside surface is hydrophobic.

17. The system of claim 16, wherein the channel is a sphering channel.

18. The system of claim 1, wherein the first structure comprises:
a channel; and
wherein the channel comprises:
an inside surface; and
wherein the inside surface is an electro-wetable surface.

19. The system of claim 18, wherein the channel is a sphering channel.

20. The system of claim 18, wherein:
the channel has a first end for an entry of a flow of a fluid;
the channel has a second end for an exit of the flow of a fluid;
the first end has a first terminal;
the second end has a second terminal; and
the first terminal and the second terminal are for an application of an electric potential.

21. The system of claim 20, wherein the inside surface has an energy change with the application of a voltage.

22. The system of claim 1, wherein the first structure comprises
a channel; and
wherein:
the channel comprises a first end and a second end;
the channel is subject to an electric field; and
the channel has an elongated dimension approximately perpendicular to the electric field.

23. The system of claim 22, wherein the channel is a sphering channel.

24. The system of claim 1, wherein the first structure comprises:
a channel; and
wherein:
the channel comprises a first end and a second end;
the channel is subject to a magnetic field; and
an elongated dimension of the channel is approximately perpendicular to the magnetic field.

25. The system of claim 24, wherein the channel is a sphering channel.

26. A cytometer comprising:
a microfluidic circuit; and
wherein:
the microfluidic circuit comprises:
a shearing mechanism; and
a sphering mechanism; and
the sphering mechanism comprises a channel for sphering red blood cells;
the shearing mechanism comprises an injector attached to the channel to form a junction for providing blood into the channel so as to produce a shear on the blood at a wall in the channel to reduce or eliminate clumping.

27. The cytometer of claim 26, wherein:
the microfluidic circuit is for providing a blood count; and
the blood count comprises red cell indices.

28. A hematology analyzer comprising:
a fluidic circuit for providing a blood count; and
wherein:
the blood count comprises a red blood count, a platelet count, mean cell volume determination of RBCs, multi-part differential counts of white blood cells (WBCs), and/or hemoglobin absorbence-based measurements; and
the fluidic circuit comprises:
a shearing mechanism;
a sphering mechanism connected to the shearing mechanism;
a sheathing mechanism;
a hydrodynamic focusing chamber connected to the sphering mechanism and the sheathing mechanism; and
an optical channel connected to the hydrodynamic focusing chamber for at least partially achieving the blood count.

29. The analyzer of claim 28, wherein
the sphering mechanism comprises a first channel for sphering red blood cells;
the shearing mechanism comprises a second channel attached to a third channel to form a T-like junction for providing blood into the third channel to produce a shear on the blood at a wall in the third channel so as to nearly eliminate clumping of blood cells; and
the first channel is connected to the third channel.

* * * * *